United States Patent
Takaku

(10) Patent No.: US 8,426,626 B2
(45) Date of Patent: Apr. 23, 2013

(54) COMPOUND HAVING ASYMMETRIC CARBON ATOM, OXIDATION-REDUCTION REACTION CAUSING PORTION, AND LIQUID CRYSTAL SUBSTITUENT

(75) Inventor: Koji Takaku, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 523 days.

(21) Appl. No.: 12/605,952

(22) Filed: Oct. 26, 2009

(65) Prior Publication Data

US 2010/0105937 A1    Apr. 29, 2010

(30) Foreign Application Priority Data

Oct. 28, 2008   (JP) .................................. 2008-277255

(51) Int. Cl.
*C07F 17/02*   (2006.01)
*G03C 1/83*   (2006.01)
*G03C 1/64*   (2006.01)

(52) U.S. Cl.
USPC ............................ 556/145; 430/521; 430/540

(58) Field of Classification Search ........................ None
See application file for complete search history.

(56) References Cited

U.S. PATENT DOCUMENTS

| | | | | |
|---|---|---|---|---|
| 4,232,950 | A | * | 11/1980 | Benham ......................... 349/165 |
| 4,495,083 | A | * | 1/1985 | Imazeki et al. ............. 252/299.1 |
| 4,780,241 | A | * | 10/1988 | Furukawa et al. ....... 252/299.63 |
| 5,422,039 | A | * | 6/1995 | Kawabata et al. ....... 252/299.62 |
| 5,668,614 | A | * | 9/1997 | Chien et al. .................... 349/115 |
| 7,722,784 | B2 | * | 5/2010 | Youfu et al. ............. 252/299.62 |
| 7,736,533 | B2 | * | 6/2010 | Takaku et al. ............ 252/299.01 |
| 7,871,539 | B2 | * | 1/2011 | Takaku et al. ............ 252/299.01 |

FOREIGN PATENT DOCUMENTS

WO    WO-02/06195 A1    1/2002

OTHER PUBLICATIONS

Bian, Z. et al. "Characteristics of selective reflection of chiral nematic liquid crystalline gels with a nonuniform pitch distribution," App. Phys. Lett., (2007) 91: 201908-1-3.*
Kikuchi, H. et al. "Polymer-stabilized liquid crystal blue phases," Nature Materials, (2002) 1: 64-68.*
Tsurutani et al., "A Light Induced Change in Cholesteric Pitch by Photoracemization of a Chiral Pyrenyl Sulfoxide" Chemistry Letters, pp. 87-88, 1999.
Mena et al., "Camphor and Nopinone Derivatives as New Photosensitive Chiral Dopants", Liquid Crystals, vol. 27, No. 7, pp. 929-933, Jan. 31, 2000.

* cited by examiner

*Primary Examiner* — Johann R Richter
*Assistant Examiner* — James Meadows
(74) *Attorney, Agent, or Firm* — Birch, Stewart, Kolasch & Birch, LLP

(57) ABSTRACT

A compound represented by the following formula is disclosed:

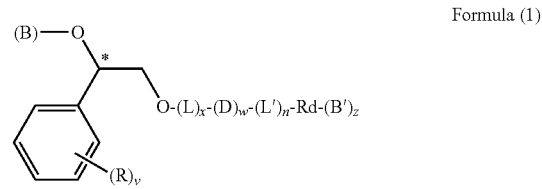

Formula (1)

In the formula, * represents an asymmetric carbon atom, L and L' independently represent an ether, ester or carbonyl group, D represents a phenylene group, R represents a substituent, B and B' independently represent liquid crystal substituents, and Rd represents an oxidation-reduction reaction causing portion, such as a substituted or unsubstituted anthraquinone or ferrocene moiety.

6 Claims, No Drawings

COMPOUND HAVING ASYMMETRIC CARBON ATOM, OXIDATION-REDUCTION REACTION CAUSING PORTION, AND LIQUID CRYSTAL SUBSTITUENT

CROSS REFERENCE TO RELATED APPLICATIONS

This application claims priority under 35 USC 119 from Japanese Patent Application No. 2008-277255 filed on Oct. 28, 2008, the disclosure of which is incorporated herein by reference.

BACKGROUND OF THE INVENTION

1. Field of the Invention

The present invention relates to a compound having an asymmetric carbon atom, an oxidation-reduction reaction causing portion, and a liquid crystal substituent.

2. Description of the Related Art

Cholesteric liquid crystals are known to exhibit structural coloration similarly as in an opal structure or a thin film interference structure. The cholesteric liquid crystals have been utilized, in the past, in thermometers utilizing temperature dependency of the structural coloration or, recently, in display materials utilizing characteristics of having memory properties in a planer phase or a focal conic phase in a liquid crystal element or lasers utilizing a refractive index periodic structure, for example.

The cholesteric liquid crystals also include nematic liquid crystals (chiral nematic phase) having a twist structure utilized in common LCDs in a broad sense. Display materials using the cholesteric liquid crystals are used for displaying document information, displaying imaging information, and light modulation for electrically controlling light.

Thus, much research on display and light modulating materials utilizing a cholesteric liquid crystal phase have been conducted heretofore. As the cholesteric liquid crystal phase, a chiral nematic phase in which a chiral reagent has been added to a nematic liquid crystal has been utilized.

An extremely large amount of research on chiral reagents has been conducted for LCD application. In general, a chiral reagent has an asymmetric carbon atom in a molecule so as to spirally arrange liquid crystal molecules and is designed by introducing a liquid crystal portion into the molecule so as to increase the compatibility of the chiral reagent with the liquid crystal (International Publication No. WO 02/06195, pamphlet).

The selective reflection length of the cholesteric liquid crystal is indicated by multiplying the pitch length and the average refractive index as illustrated in the following Equation.

$$\lambda = P \cdot n \quad \text{Equation}$$

In the Equation above, P represents the pitch length, and n represents the average refractive index of the liquid crystal.

In toning of the structural color by the cholesteric liquid crystal, changes in the pitch length in the liquid crystal orientation direction are utilized, unlike in the case of the opal structure or the thin film interference structure. Therefore, there is an advantage in that volume changes do not accompany this utilization. Attempts to change the pitch length by external stimulus have been studied, and methods for changing the pitch length by heat or light have been proposed in Chemistry Letters, 199, 87-88 (1999) and Liquid Crystals, 27, 929-933 (2000).

SUMMARY OF THE INVENTION

A first aspect of the present invention is a compound represented by the following Formula (1).

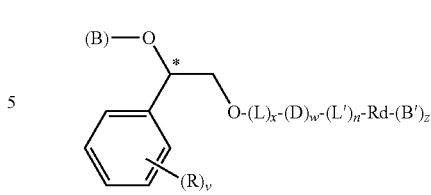

Formula (1)

In Formula (1), * represents an asymmetric carbon atom; L and L' each independently represent a divalent linking group; Rd represents an oxidation-reduction reaction causing portion; B and B' each independently represent a liquid crystal substituent; D represents an arylene group, a hetero arylene group, or a divalent alicyclic hydrocarbon group; R represents a substituent; x represents 0 or 1; z represents an integer of from 0 to 3; w represents 0 or 1; n represents 0 or 1; v represents an integer of from 0 to 5; when z is 2 or more, a plural B's may be the same or different; and when v is 2 or more, a plural R's may be the same or different.

DETAILED DESCRIPTION OF THE INVENTION

The present inventors have repeatedly conducted extensive research, and as a result, found a breakthrough phenomenon in which a selective reflection wavelength changes with a low voltage and a high response rate by applying an electric field to a cholesteric liquid crystal phase exhibiting selective reflection to cause an oxidation-reduction reaction of a chiral dopant.

Therefore, a chiral dopant causing an oxidation-reduction reaction suitable for an element utilizing this phenomenon has been desired.

The present inventors have conducted further extensive researches, and created a novel compound particularly useful as the dopant causing an oxidation-reduction reaction. The dopant can also be applied to display modes, such as a guest host display system (White-Taylor display system) using a dichromatic coloring material. When the dopant has an anthraquinone structure, the dopant can be used as a UV absorber.

Hereinafter, the present invention will be described in detail. In this description, "to" indicates a range including the numerical values indicated before and after "to" as the minimum value and the maximum value, respectively.

The novel compound of the present invention is represented by the following Formula (1).

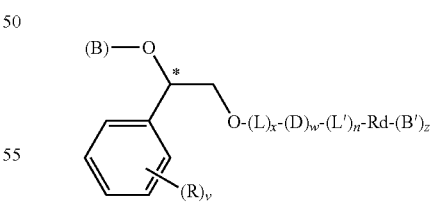

Formula (1)

In Formula (1), * represents an asymmetric carbon atom; L and L' each independently represent a divalent linking group; Rd represents an oxidation-reduction reaction causing portion; B and B' each independently represent a liquid crystal substituent; D represents an arylene group, a hetero arylene group, or a divalent alicyclic hydrocarbon group; R represents a substituent; x represents 0 or 1; z represents an integer of from 0 to 3; w represents 0 or 1; n represents 0 or 1; and v represents an integer of from 0 to 5.

When z is 2 or more, plural B's may be the same or different. When v is 2 or more, plural R's may be the same or different.

In Formula (1), L and L' each independently represent a divalent linking group. Preferably, L and L' each independently represent an ether group, an ester group (—COO—, —OCO—), or a carbonyl group, and more preferably a carbonyl group.

L and L' may be the same or different, but when w is 0, L and L' represent different linking groups.

Rd in Formula (1) represents an oxidation-reduction reaction causing portion. Preferably, the oxidation-reduction reaction causing portion refers to a portion where oxidation or reduction of two or more electrons occurs. Specific examples thereof include ferrocene, anthraquinone, viologen, derivatives thereof, and organometallic complexes (for example, a copper I complex, a copper II complex, a ruthenium complex); and ferrocene, anthraquinone, and derivatives thereof are preferable. In the present specification, the term "derivative" indicates compounds which have been subjected to substitution, addition or the like, for the purpose of adjusting the oxidation-reduction potential or the solubility in liquid crystals of ferrocene or anthraquinone.

Among the above, it is preferable that Rd be anthraquinone or an anthraquinone derivative, from the viewpoint that oxidation or reduction of two or more electrons occurs and interaction changes with a host liquid crystal are enhanced. In the case of anthraquinone or an anthraquinone derivative, the compound represented by Formula (1) can also be used as a UV absorber.

When Rd is anthraquinone or an anthraquinone derivative, the connecting position of ≡C*—CH$_2$—O-(L)$_x$-(D)$_w$-(L')$_n$-*1 (*1 represents a connecting position with Rd) in Formula (1) is preferably 5-position, 6-position, 7-position, or 8-position of the anthraquinone or the anthraquinone derivative, more preferably 6-position or 7-position, and still more preferably 7-position.

When Rd is anthraquinone or an anthraquinone derivative, the connecting position of —(B')$_z$ in Formula (1) is preferably 1-position, 2-position, 3-position, or 4-position of the anthraquinone or the anthraquinone derivative. When the connecting position of ≡C*—CH$_2$—O-(L)$_x$-(D)$_w$-(L')$_n$-*1 is 6-position, the connecting position of —(B')$_z$ is preferably 2-position or 3-position. When —(B')$_z$ is an arylthio group, the connecting position of —(B')$_z$ is preferably 1-position or 4-position.

Therefore, when Rd is anthraquinone or an anthraquinone derivative, the following Formula (1-1) or (1-2) is preferable.

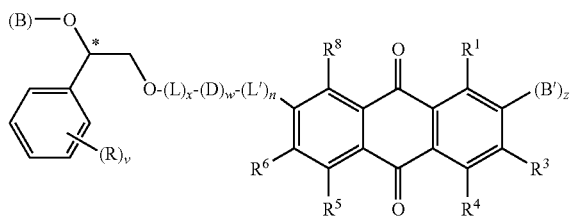

Formula (1-1)

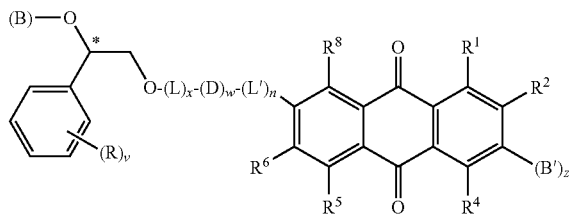

Formula (1-2)

L, L', R, B, B', D, x, z, n, w, and v in Formula (1-1) or (1-2) are the same as L, L', R, B, B', D, x, z, n, w, and v in Formula (1), respectively.

In Formulae (1-1) and (1-2), R', R$^2$, R$^3$, R$^4$, R$^5$, R$^6$, and R$^8$ each independently represent a hydrogen atom or a substituent. Examples of the substituent include substituents of the substituent group V described later.

Preferably, R', R$^2$, R$^3$, R$^4$, R$^5$, R$^6$, and R$^8$ each independently represent a hydrogen atom, an aryl group, an alkyl group, an alkoxy group, a hydroxy group, ester (—CO$_2$—, —OCO—), amide (—NHCO—, —CONH—), an arylthio group, or a halogen atom.

It is preferable that Rd be ferrocene or a ferrocene derivative, from the viewpoint of durability against oxidation reduction. When Rd is ferrocene or a ferrocene derivative, the compound represented by Formula (1) can also be used as a UV absorber.

When Rd is ferrocene or a ferrocene derivative, the connecting position of ≡C*—CH$_2$—O-(L)$_x$-(D)$_w$-(L')$_n$-*1 (*1 represent a connecting position with Rd) in Formula (1) may be attached to any of ferrocene or a ferrocene derivative.

When Rd is ferrocene or a ferrocene derivative, the connecting position of —(B')$_z$ in Formula (1) may be present on the same cyclopentadienyl ring or may be on another cyclopentadienyl ring relative to the connecting position of ≡C*—CH$_2$—O-(L)$_x$-(D)$_w$-(L')$_n$-*1. When the connecting position of —(B') z is present on the same cyclopentadienyl ring of ≡C*—CH$_2$—O-(L)$_x$-(D)$_w$-(L')$_n$-*1, the connecting position of —(B') z is preferably 3-position or 4-position when the connecting position of *1 is 1-position.

Therefore, when Rd is ferrocene or a ferrocene derivative, Formula (1-3) or (1-4) is preferable.

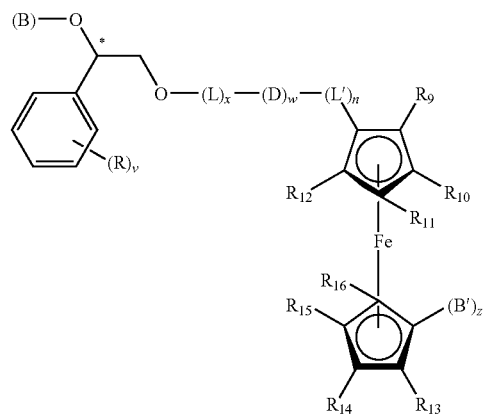

Formula (1-3)

-continued

Formula (1-4)

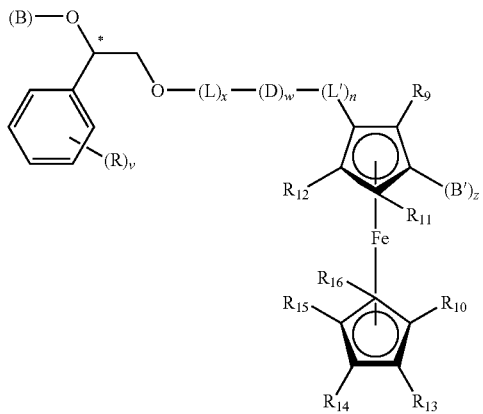

L, L', R, B, B', D, x, z, n, w, and v in Formula (1-3) or (1-4) are the same as L, L', R, B, B', D, x, z, n, w, and v in Formula (1), respectively.

In Formulae (1-3) and (1-4), $R^9$, $R^{10}$, $R^{11}$, $R^{12}$, $R^{13}$, $R^{14}$, $R^{15}$, and $R^{16}$ each independently represent a hydrogen atom or a substituent. Examples of the substituent include substituents of the substituent group V described later.

Preferably, $R^9$, $R^{10}$, $R^{11}$, $R^{12}$, $R^{13}$, $R^{14}$, $R^{15}$, and $R^{16}$ each independently represent a hydrogen atom, an alkyl group, ester (—$CO_2$—), and amide (—CONH—).

When an electric field is applied to a cholesteric liquid crystal using the compound represented by Formula (1) as a chiral dopant, the oxidation-reduction potential of Rd in Formula (1) is preferably from −2.5 V to 0 V (reduction potential) and from 0 V to +2.5 V (oxidation potential), more preferably from −2.2 V to −0.2 V and from +0.1 V to +1.8 V, and still more preferably from −1.8 V to −0.4 V and from +0.3 V to +1.0 V relative to the reference electrode SCE, from the viewpoint of changing the selective reflection wavelength with a low voltage and a high response rate.

B and B' in Formula (1) each independently represent a liquid crystal substituent. There is no limitation on the liquid crystal substituent insofar as it exhibits interaction with a host liquid crystal, and exhibits a cholesteric phase in the shape of a chiral dopant. The liquid crystal substituent refers to a substituent having two or more cyclic structures, such as cyclohexane or a benzene ring, and refers to one having a structure similar to compounds exhibiting liquid crystallinity.

Examples of the compounds exhibiting liquid crystallinity include liquid crystal compounds exhibiting a nematic phase or a smectic phase. Specific examples include azomethine compounds, cyanobiphenyl compounds, cyanophenyl esters, fluorine-substituted phenyl esters, cyclohexanecarboxylic acid phenyl esters, fluorine-substituted cyclohexanecarboxylic acid phenyl esters, cyanophenyl cyclohexanes, fluorine-substituted phenylcyclohexanes, cyano-substituted phenylpyrimidines, fluorine-substituted phenylpyrimidines, alkoxy-substituted phenylpyrimidines, fluorine-substituted alkoxy-substituted phenylpyrimidines, phenyldioxanes, tolan compounds, fluorine-substituted tolan compounds, and alkenyl cyclohexylbenzonitriles.

The details are described in "Ekisho Debaisu Handobukku (Liquid Crystal Device Handbook)" edited by No. 142 Committee of Japan Society for the Promotion of Science, published by Nikkan Kogyo Shimbun Ltd., 1989, pages 154 to 192 and 715 to 722.

In Formula (1), it is preferable that the liquid crystal substituents B and B' each be independently represented by the following Formula (2).

$$T^1\text{-}(D^2)_k\text{-}((L^1)_f\text{-}(D^1)_e)_m\text{-}(L^2)_g\text{-}((CH_2)_i\text{-}L^3)_t\text{-}*1 \qquad \text{Formula (2)}$$

In Formula (2), *1 represents a connecting position with O (in the case of substituent B) or Rd (in the case of substituent B') in Formula (1); $D^1$ and $D^2$ each independently represent an arylene group, a hetero arylene group, or a divalent alicyclic hydrocarbon group; $L^1$, $L^2$, and $L^3$ each independently represent a divalent linking group; $T^1$ represents an alkyl group, an alkoxy group, an alkoxycarbonyl group, an acyl group, an acyloxy group, a halogen atom, or a cyano group; e represents an integer of from 1 to 3; f represents an integer of from 0 to 2; m represents an integer of from 1 to 3; k represents 1 or 2; g represents 0 or 1; i represents an integer of from 1 to 20; t represents an integer of from 0 to 4; and the total number of the groups represented by $D^1$ and $D^2$ is an integer of from 2 to 5. When e or k is 2 or more, two or more groups represented by $D^1$ or $D^2$ may be the same or different. When m is 2 or more, two or more groups represented by $((L^1)_f\text{-}(D^1)_e)$ may be the same or different. When f is 2, two groups represented by $L^1$ each represent different linking groups. When t is 2 or more, two or more groups represented by $((CH_2)_i\text{-}L^3)$ each may be the same or different.

In Formula (2), the arylene groups represented by $D^1$ and $D^2$ are preferably arylene groups having 6 to 20 carbon atoms, and more preferably 6 to 10 carbon atoms. Specific examples of preferable arylene groups include phenylene groups and naphthalene groups, for example, a 1,4-phenylene group, a naphthalene-2,6-diyl group, and a tetrahydronaphthalene-2,6-diyl group.

In Formula (2), the heteroarylene groups represented by $D^1$ and $D^2$ are preferably heteroarylene groups having 1 to 20 carbon atoms, and more preferably 2 to 9 carbon atoms. Specific examples of preferable heteroarylene groups include heteroarylene groups obtained by removal of one hydrogen atom from each of two carbon atoms of a pyridine ring, a quinoline ring, an isoquinoline ring, a pyrimidine ring, a pyrazine ring, a thiophene ring, a furan ring, an oxazole ring, a thiazole ring, an imidazole ring, a pyrazole ring, an oxadiazole ring, a thiadiazole ring, a triazole ring and a condensed ring resulting from condensation of those rings.

In Formula (2), the divalent alicyclic hydrocarbon groups represented by $D^1$ and $D^2$ are preferably divalent alicyclic hydrocarbon groups having 3 to 20 carbon atoms, and more preferably 4 to 12 carbon atoms. Specific examples of preferable divalent alicyclic hydrocarbon groups include cyclohexanediyl, decahydronaphthalenediyl, and spiro[5.5]undecylene, and more preferably examples include a cycrohexane-1,4-diyl group, a decahydronaphthalene-2,6-diyl group, and a 3,9-spiro[5.5]undecylene group.

In Formula (2), the arylene groups, the heteroarylene groups and the divalent alicyclic hydrocarbon groups represented by $D^1$ and $D^2$ may be either substituted or unsubstituted. In Formula (2), when e, m or k is 2 or more, plural $D^1$s and $D^2$s each independently may have a substituent. They may have the same substituents, different substituents, or no substitutes.

Examples of the substituents include the following substituent group V.

(Substituent Group V)

Examples include halogen atoms (for example, chlorine, bromine, iodine, and fluorine), a mercapto group, a cyano group, a carboxyl group, a phosphate group, a sulfo group, a hydroxy group, carbamoyl groups having 1 to 10 carbon atoms, preferably 2 to 8 carbon atoms, and more preferably 2 to 5 carbon atoms (for example, methylcarbamoyl, ethylcarbamoyl, and morpholinocarbonyl), sulfamoyl groups having 0 to 10 carbon atoms, preferably 2 to 8 carbon atoms, and more preferably 2 to 5 carbon atoms (for example, methyl sulfamoyl, ethyl sulfamoyl, and piperidino sulfonyl), a nitro group, alkoxy groups having 1 to 20 carbon atoms, preferably 1 to 10 carbon atoms, and more preferably 1 to 8 carbon atoms (for example, methoxy, ethoxy, 2-methoxyethoxy, and 2-phenylethoxy), aryl oxy groups having 6 to 20 carbon atoms, preferably 6 to 12 carbon atoms, and more preferably 6 to 10 carbon atoms (for example, phenoxy, p-methylphenoxy, p-chlorophenoxy, and naphthoxy), acyl groups having 1 to 20 carbon atoms, preferably 2 to 12 carbon atoms, and more preferably 2 to 8 carbon atoms, (for example, acetyl, benzoyl, and trichloroacetyl), acyloxy groups having 1 to 20 carbon atoms, preferably 2 to 12 carbon atoms, and more preferably 2 to 8 carbon atoms (for example, acetyloxy and benzoyloxy), acylamino groups having 1 to 20 carbon atoms, preferably 2 to 12 carbon atoms, and more preferably 2 to 8 carbon atoms (for example, acetylamino), sulfonyl groups having 1 to 20 carbon atoms, preferably 1 to 10 carbon atoms, and more preferably 1 to 8 carbon atoms (for example, methanesulfonyl, ethanesulfonyl, and benzenesulphonyl), sulfinyl groups having 1 to 20 carbon atoms, preferably 1 to 10 carbon atoms, and more preferably 1 to 8 carbon atoms (for example, methanesulfinyl, ethanesulfinyl, and benzenesulfinyl), substituted or unsubstituted amino groups having 1 to 20 carbon atoms, preferably 1 to 12 carbon atoms, and more preferably 1 to 8 carbon atoms (for example, amino, methylamino, dimethylamino, benzylamino, anilino, diphenylamino, 4-methylphenylamino, 4-ethylphenylamino, 3-n-propylphenylamino, 4-n-propylphenylamino, 3-n-butylphenylamino, 4-n-butylphenylamino, 3-n-pentylphenylamino, 4-n-pentylphenylamino, 3-trifluoromethyl phenylamino, 4-trifluoromethyl phenylamino, 2-pyridylamino, 3-pyridylamino, 2-thiazolyl amino, 2-oxazolylamino, N,N-methylphenylamino, and N,N-ethylphenylamino), ammonium groups having 0 to 15 carbon atoms, preferably 3 to 10 carbon atoms, and more preferably 3 to 6 carbon atoms (for example, trimethylammonium and triethylammonium), hydrazino groups having 0 to 15 carbon atoms, preferably 1 to 10 carbon atoms, and more preferably 1 to 6 carbon atoms (for example, a trimethyl hydrazino group), ureido groups having 1 to 15 carbon atoms, preferably 1 to 10 carbon atoms, and more preferably 1 to 6 carbon atoms (for example, an ureido group and an N,N-dimethyl ureido group), imido groups having 1 to 15 carbon atoms, preferably 1 to 10 carbon atoms, and more preferably 1 to 6 carbon atoms (for example, a succinimide group), alkylthio groups having 1 to 20 carbon atoms, preferably 1 to 12 carbon atoms, and more preferably 1 to 8 carbon atoms (for example, methylthio, ethylthio, and propylthio), arylthio groups having 6 to 80 carbon atoms, preferably 6 to 40 carbon atoms, and more preferably 6 to 30 carbon atoms (for example, phenylthio, p-methylphenylthio, p-chlorophenylthio, 2-pyridylthio, 1-naphthylthio, 2-naphthylthio, 4-propylcyclohexyl-4'-biphenylthio, 4-butylcyclohexyl-4'-biphenylthio, 4-pentylcyclohexyl-4'-biphenylthio, and 4-propylphenyl-2-ethynyl-4'-biphenylthio), heteroarylthio groups having 1 to 80 carbon atoms, preferably 1 to 40 carbon atoms, and more preferably 1 to 30 carbon atoms (for example, 2-pyridylthio, 3-pyridylthio, 4-pyridylthio, 2-quinolylthio, 2-furylthio, and 2-pyrrolylthio), alkoxycarbonyl groups having 2 to 20 carbon atoms, preferably 2 to 12 carbon atoms, and more preferably 2 to 8 carbon atoms (for example, methoxycarbonyl, ethoxycarbonyl, and 2-benzyloxycarbonyl), aryloxy carbonyl groups having 6 to 20 carbon atoms, preferably 6 to 12 carbon atoms, and more preferably 6 to 10 carbon atoms (for example, phenoxycarbonyl), unsubstituted alkyl groups having 1 to 18 carbon atoms and preferably 1 to 10 carbon atoms (for example, methyl, ethyl, propyl, and butyl, and, here, including alicyclic hydrocarbons (cyclohexane and the like), substituted alkyl groups having 1 to 18 carbon atoms and preferably 1 to 10 carbon atoms {for example, hydroxymethyl, trifluoromethyl, benzyl, carboxyethyl, ethoxy carbonylmethyl, and acetyl aminomethyl, and, here, unsaturated hydrocarbon groups having 2 to 18 carbon atoms, preferably 3 to 10 carbon atoms, and more preferably 3 to 5 carbon atoms (for example, a vinyl group, an ethynyl group, a 1-cyclohexenyl group, a benzylidyne group, and a benzylidene group) are also included in the substituted alkyl groups}, substituted or unsubstituted aryl groups having 6 to 20 carbon atoms, preferably 6 to 15 carbon atoms, and more preferably 6 to 10 carbon atoms (for example, phenyl, naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, and 4-propylphenyl-2-ethynyl-4'-biphenyl), and substituted or unsubstituted heteroaryl groups having 1 to 20 carbon atoms, preferably 2 to 10 carbon atoms, and more preferably 4 to 6 carbon atoms (for example, pyridyl, 5-methylpyridyl, thienyl, furyl, morpholino, and tetrahydrofurfuryl).

The substituents of the substituent group V may have a structure in which a benzene ring or a naphthalene ring has been condensed. Furthermore, the substituents mentioned in the description of the group V described above may be substituted on these substituents.

Among the substituent group V, preferable substituents as the substituents of the divalent arylene groups and the divalent hetero arylene group and the divalent alicyclic hydrocarbon groups represented by $D^1$ and $D^2$ are alkyl groups, alkoxy groups, halogen atoms, and cyano groups.

In Formula (2), $L^1$ represents a divalent linking group. Preferable examples thereof include alkanediyl groups, alkenylene groups, alkynylene groups, ether groups, ester groups (—COO—, —OCO—), carbonyl groups, azo groups (—CH=N—, —N=CH—), azoxy groups, and alkyleneoxy groups, and more preferable examples include alkanediyl groups (for example, an ethylene group), alkynylene groups (for example, an ethynylene group), ester groups, and alkyleneoxy groups (for example, a methyleneoxy group).

In Formula (2), $T^1$ represents an alkyl group, an alkoxy group, an alkoxycarbonyl group, an acyl group, an acyloxy group, a halogen atom, or a cyano group.

Preferable examples of $T^1$ include alkyl groups having 1 to 30 carbon atoms, preferably 3 to 20 carbon atoms, and more preferably 3 to 10 carbon atoms (for example, an n-propyl group, an n-butyl group, an n-pentyl, an n-hexyl group hydroxymethyl, trifluoromethyl, benzyl, carboxyethyl, ethoxy carbonylmethyl, acetyl aminomethyl, and, here, unsaturated hydrocarbon groups having 2 to 18 carbon atoms and preferably 3 to 10 carbon atoms (for example, a vinyl group, an ethynyl group, a 1-cyclohexenyl group, a benzylidyne group, and a benzylidene group) also being included in the substituted alkyl groups); alkoxy groups having 1 to 30 carbon atoms, more preferably 3 to 20 carbon atoms, and more preferably 3 to 10 carbon atoms (for example, an n-propyloxy group, an n-butoxy group, an n-pentyloxy group, and an n-hexyloxy group); and halogen atoms (for example, a fluorine atom and a chlorine atom).

The alkyl group, the alkoxy group, the alkoxycarbonyl group, the acyl group, and the acyloxy group represented by $T^1$ in Formula (2) may or may not have a substituent. Examples of the substituent include the substituent group V described above.

The substituents of the alkyl group, the alkoxy group, the alkoxycarbonyl group, the acyl group, and the acyloxy group represented by $T^1$ are preferably halogen atoms (particularly a chlorine atom and a fluorine atom), cyano groups, hydroxy groups, alkoxy groups, or acyl groups among the substituent group V.

In Formula (2), $T^1$ may be connected to any positions of $D^2$, and preferably 4-position of $D^2$ (i.e., para-position).

In Formula (2), e represents an integer of from 1 to 3, and preferably 1 or 2. When e represents 2 or 3, plural $D^1$'s may be the same or different.

In Formula (2), m represents an integer of from 1 to 3, and preferably 1 or 2. When m represents 2 or 3, plural $D^1$'s may be the same or different, and plural $L^1$'s may be the same or different.

In Formula (2), k is 1 or 2. When k is 2, plural $D^2$s may be the same or different.

In Formula (2), f is an integer of from 0 to 2, and preferably 0 or 1. When f is 2, plural $L^1$s each represent different linking groups.

In Formula (2), the total number of the groups represented by $D^1$ and $D^2$, i.e., e×m+k, is an integer of from 2 to 5, more preferably an integer of from 2 to 4, and particularly preferably an integer of from 2 to 3. When e or k is 2 or more, two or more $D^1$ or $D^2$ may be the same or different. When m is 2 or more, two or more $((L^1)_f\text{-}(D^1)_e)$'s each may be the same or different.

Particularly preferable combinations of e, f, m, and k are described below.
(I) e=1, f=0, m=1, and k=1
(II) e=1, f=1, m=1, and k=1
(III) e=1, f=0, m=2, and k=1
(IV) e=2, f=1, m=1, and k=1
(V) e=1, f=1, m=1, and k=2
(VI) e=1, f=1, m=2, and k=1
(VII) e=2, f=1, m=1, and k=2

In Formula (2), $L^2$ represents a divalent linking group. Preferably, $L^2$ represents an ether group, an ester group (—COO—, —OCO—), or a carbonyl group.

In Formula (2), $L^3$ represents a divalent linking group. Preferably, $L^3$ represents an ether group, an ester group (—COO—, —OCO—), or a carbonyl group.

In Formula (2), g is 0 or 1.

In Formula (2), i represents an integer of from 1 to 20, and preferably from 1 to 11.

In Formula (2), t represents an integer of from 0 to 4, and preferably from 1 to 3. When t is 2 or more, plural $((CH_2)_i\text{-}L^3)$'s may be the same or different, and is may be the same number or a different number.

In Formula (1), D represents an arylene group, a heteroarylene group or a divalent alicyclic hydrocarbon group, and may or may not have a substituent. Examples of the substituent include the substituent group V described above. Among the substituent group V, substituted or unsubstituted alkyl groups, aryl groups, cyano groups, esters (an acyloxy group, an alkoxycarbonyl group, and an aryloxy carbonyl group), ethers (an alkoxy group and an aryl oxy group), amides (a carbamoyl group and an acylamino group), nitro groups, alkylamino groups, arylamino groups, hydroxy groups, or halogen atoms are preferable. More preferably, D is not substituted, or has a substituted or unsubstituted alkyl group, cyano group, ether (an alkoxy group or an aryl oxy group), nitro group, hydroxy group, or halogen atom.

In Formula (1), the arylene group represented by D is preferably an arylene group having 6 to 20 carbon atoms, and more preferably 6 to 10 carbon atoms. Specific examples of preferable arylene groups include phenylene groups and naphthalene groups, and examples include a 1,4-phenylene group, a naphthalene-2,6-diyl group, and a tetrahydronaphthalene-2,6-diyl group.

The hetero arylene group represented by D is preferably a heteroarylene group having 1 to 20 carbon atoms, and more preferably 2 to 9 carbon atoms. Specific examples of preferable heteroarylene groups include heteroarylene groups obtained by removal of one hydrogen atom from each of two carbon atoms of a pyridine ring, a quinoline ring, an isoquinoline ring, a pyrimidine ring, a pyrazine ring, a thiophene ring, a furan ring, an oxazole ring, a thiazole ring, an imidazole ring, a pyrazole ring, an oxadiazole ring, a thiadiazole ring, a triazole ring, and a condensed ring resulting from condensation of those rings.

The divalent alicyclic hydrocarbon group represented by D is preferably a divalent alicyclic hydrocarbon group having 3 to 20 carbon atoms, and more preferably 4 to 12 carbon atoms. Specific examples of preferable divalent alicyclic hydrocarbon groups include cyclohexanediyl, decahydronaphthalenediyl, and spiro[5.5]undecylene, and more preferably a cycrohexane-1,4-diyl group, a decahydronaphthalene-2,6-diyl group, and a 3,9-spiro[5.5]undecylene group.

In Formula (1), R represents a substituent, and examples thereof include the substituents of the substituent group V described above. Among the substituent group V, as R in Formula (1), substituted or unsubstituted alkyl groups (also including alicyclic hydrocarbons), aryl groups, cyano groups, esters (for example, an acyloxy group, an alkoxycarbonyl group, and an aryloxy carbonyl group), ethers (an alkoxy group and an aryl oxy group), amides (a carbamoyl group and an acylamino group), nitro groups, alkylamino groups, arylamino groups, hydroxy groups, or halogen atoms are preferable; and substituted or unsubstituted alkyl groups (also including alicyclic hydrocarbon), aryl groups, cyano groups, esters (for example, an acyloxy group, an alkoxycarbonyl group, and an aryloxy carbonyl group), ethers (for example, an alkoxy group and an aryl oxy group), or halogen atoms are more preferably.

The alkyl group represented by R in Formula (1) has preferably 1 to 20 carbon atoms, more preferably 1 to 16 carbon atoms, and particularly preferably 1 to 14 carbon atoms.

The aryl group represented by R in Formula (1) has preferably 6 to 24 carbon atoms, more preferably 6 to 20 carbon atoms, and particularly preferably 6 to 18 carbon atoms.

In Formula (1), x is 0 or 1, and preferably 1.

In Formula (1), z represents an integer of from 0 to 3, preferably an integer of from 0 to 2, and more preferably 0 or 1.

In Formula (1), n represents 0 or 1.

In Formula (1), w represents 0 or 1.

In Formula (1), v represents an integer of from 0 to 5, preferably an integer of from 0 to 3, and more preferably an integer of from 0 to 2.

Examples of preferable compounds represented by Formula (1) are compounds represented by the following Formula (3-1), (3-2), (3-3), or (3-4).

Formula (3-1)

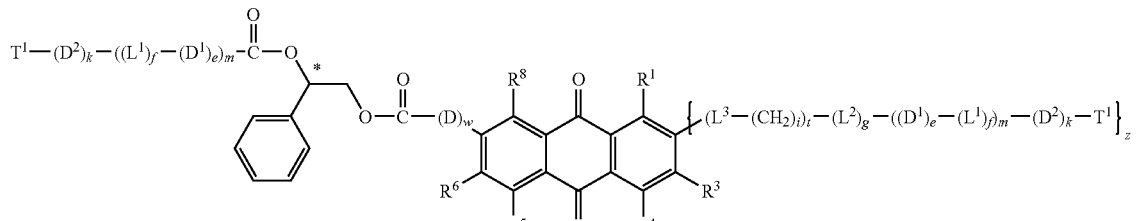

Formula (3-2)

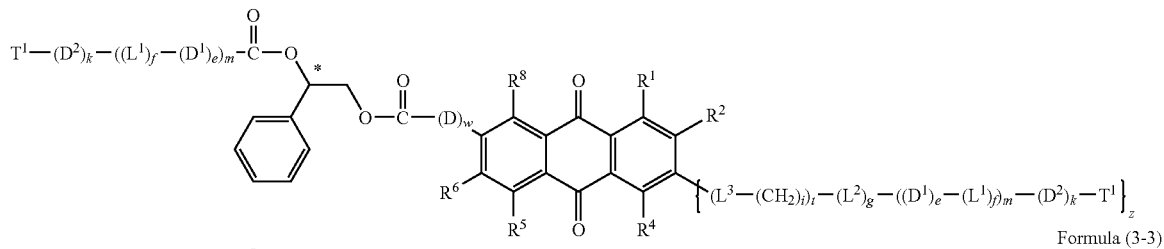

Formula (3-3)

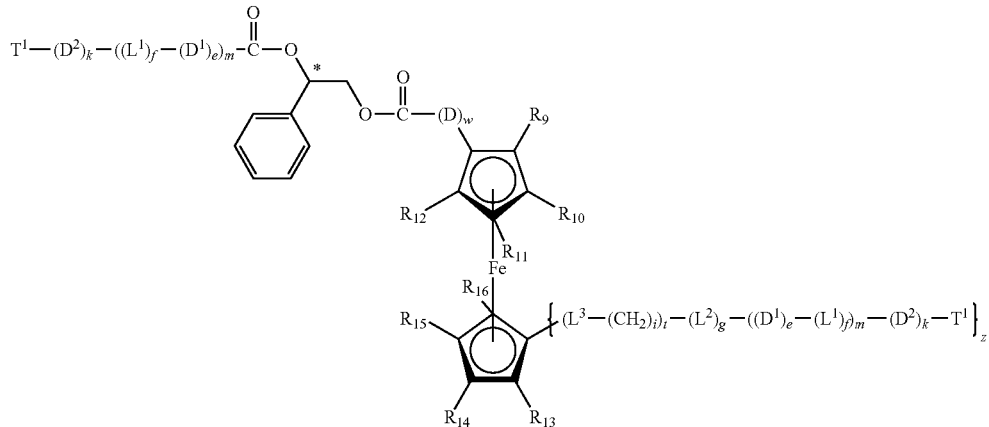

Formula (3-4)

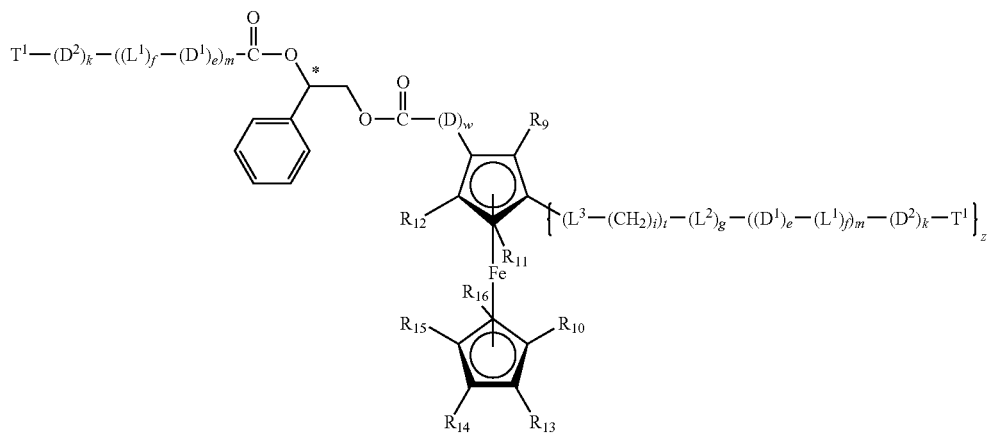

In Formulae (3-1), (3-2), (3-3) and (3-4), D, w and z are the same as D, w and z in Formula (1), respectively; $T^1$, $D^1$, $D^2$, $L^1$, $L^2$, $L^3$, e, f, g, k, m, i and t are the same as $T^1$, $D^1$, $D^2$, $L^1$, $L^2$, $L^3$, e, f, g, k, m, i and t in Formula (2), respectively; and $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$ and $R^{16}$ are the same as $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$ and $R^{16}$ in Formulae (1-1), (1-2), (1-3), and (1-4), respectively.

Specific examples of the compound represented by Formula (1) in the present invention are shown below, but the present invention is not limited thereto.

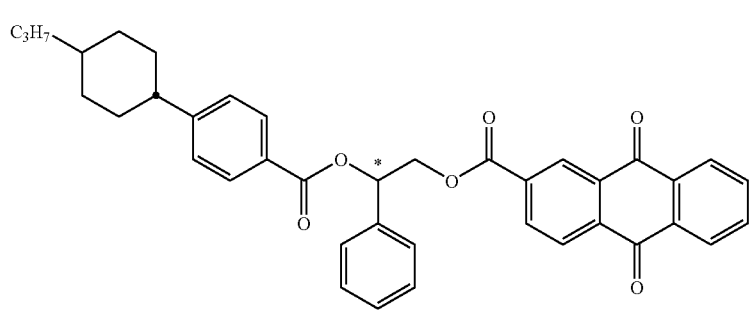
(1)
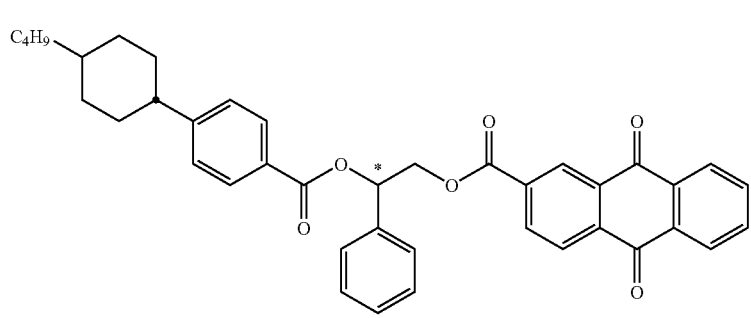
(2)
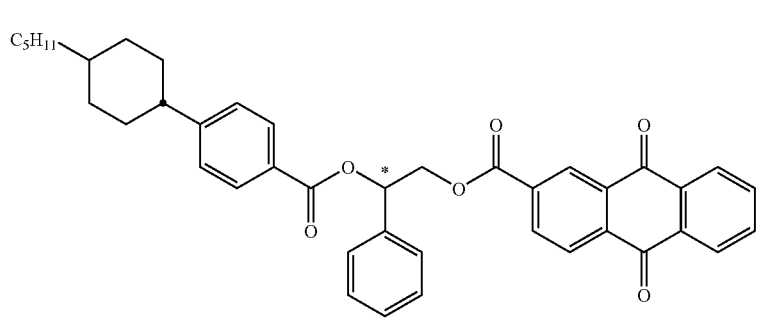
(3)
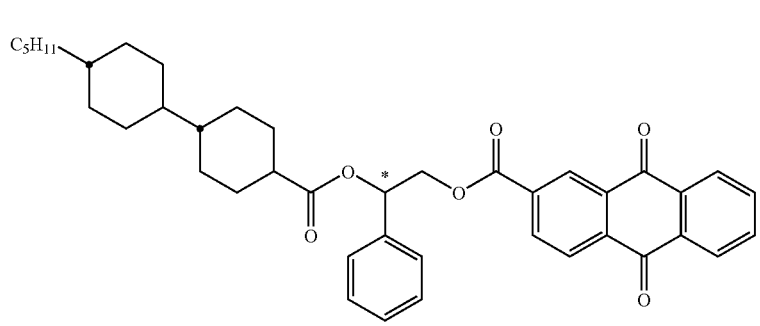
(4)
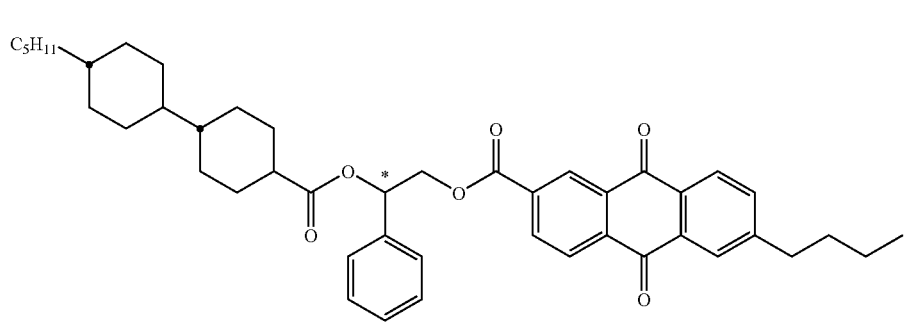
(5)

(6)
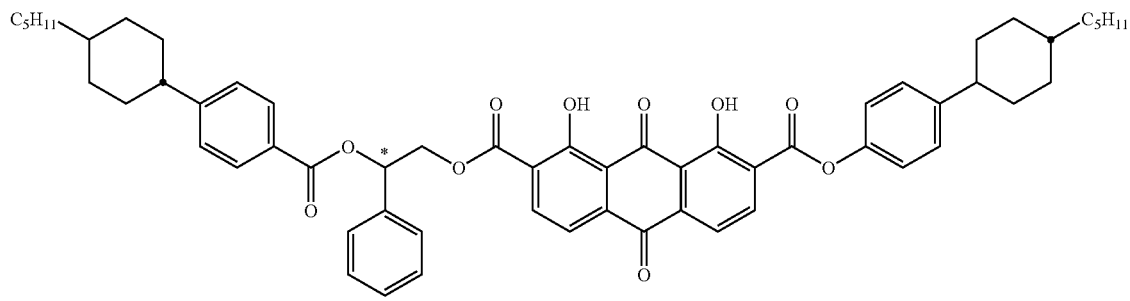
(7)
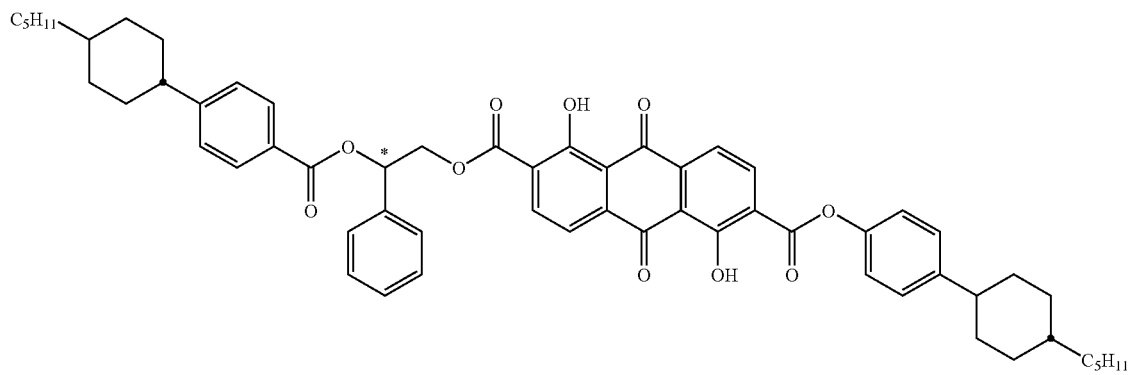
(8)
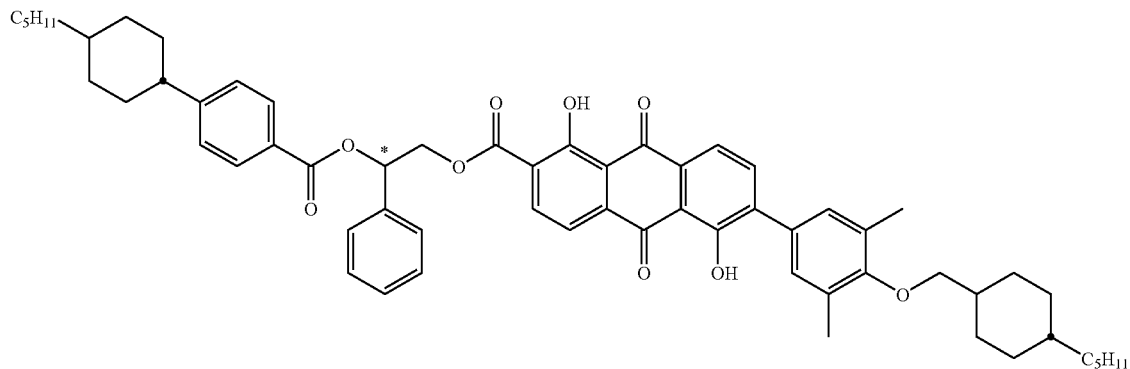
(9)
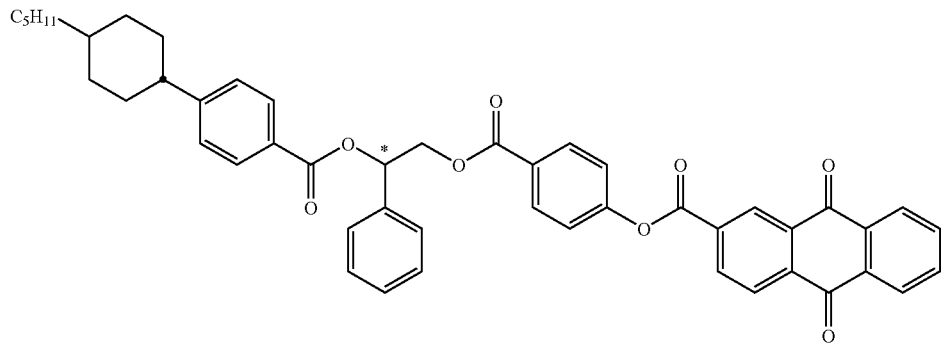

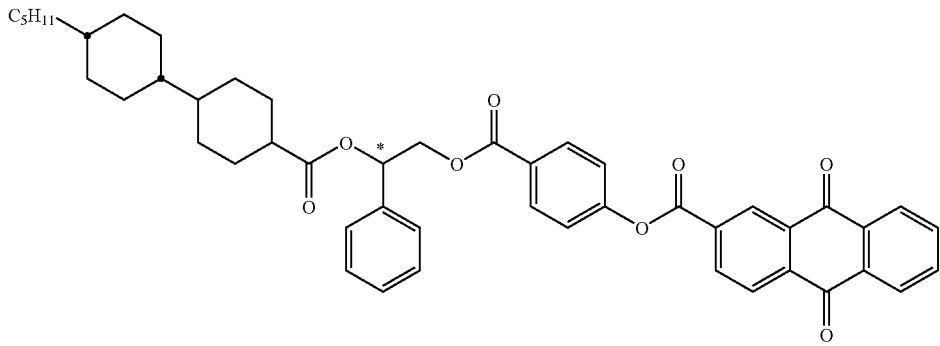
(10)
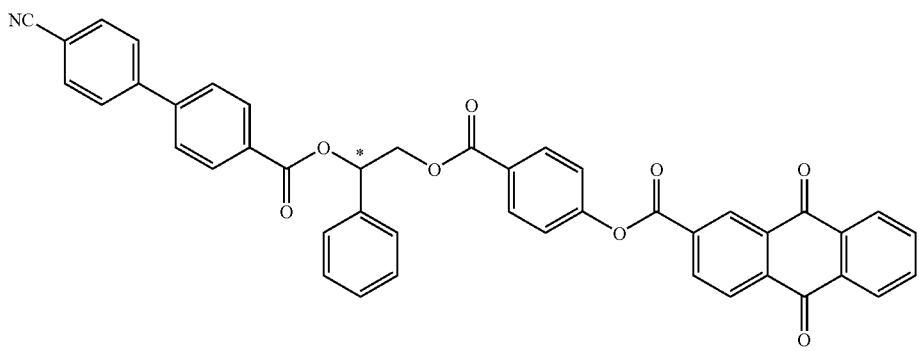
(11)
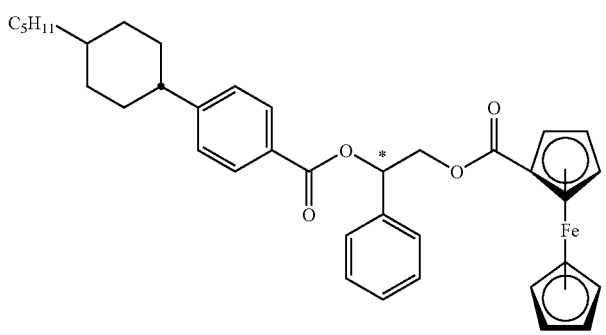
(12)
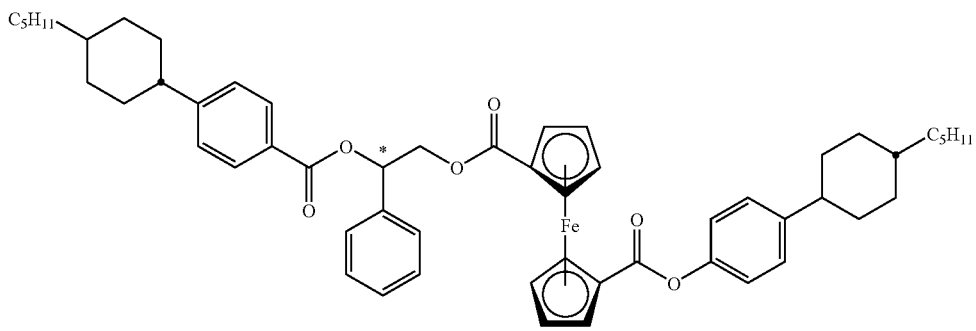
(13)

-continued
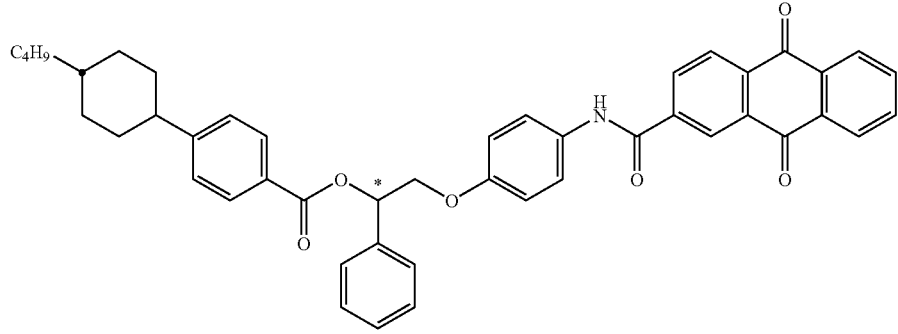
(14)
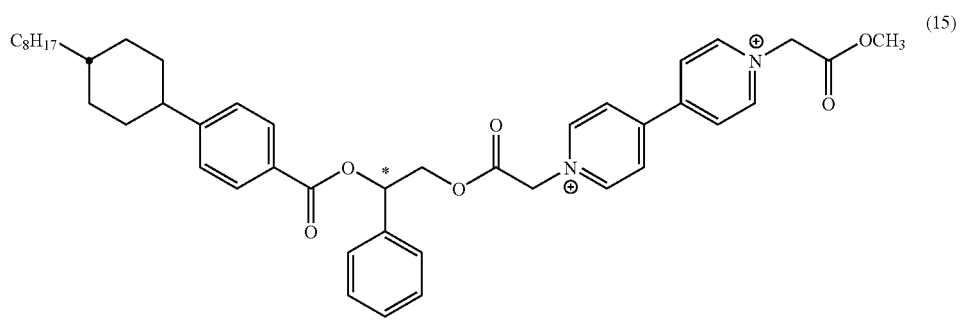
(15)
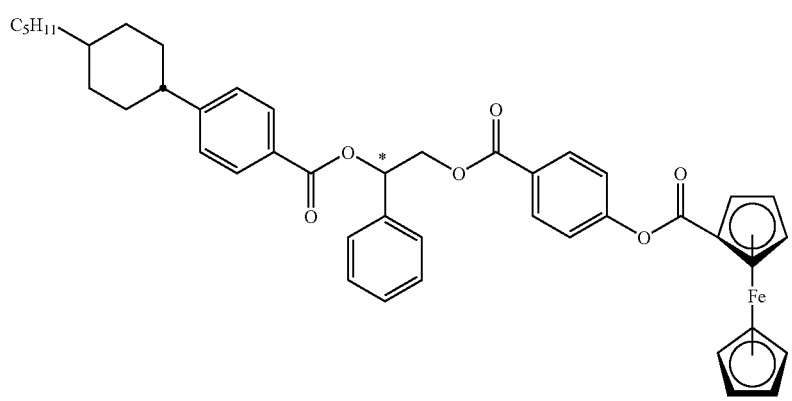
(16)
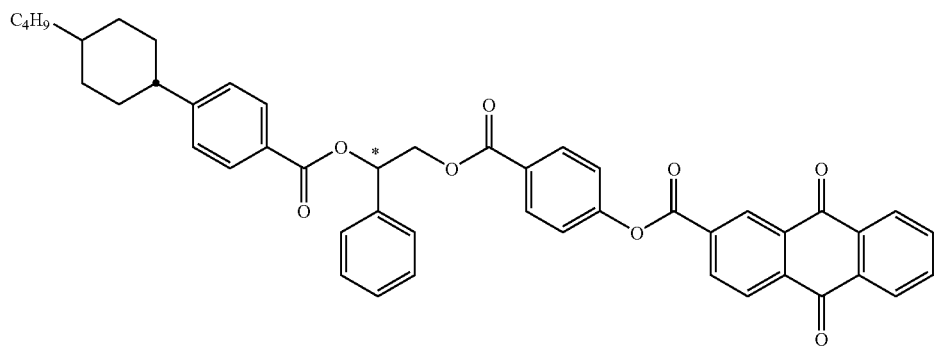
(17)

-continued (18)

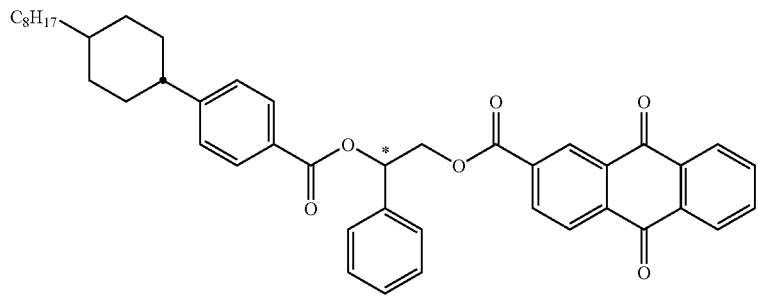

(19)

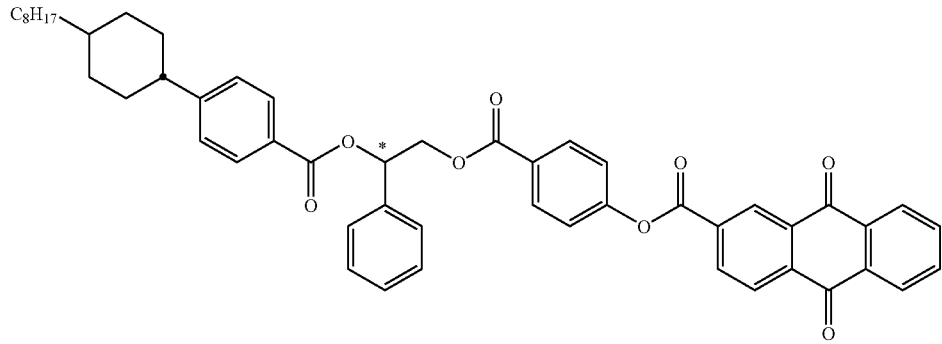

EXAMPLES

Hereinafter, the present invention will be described in more detail. The Examples describe the present invention, and the present invention is not limited to the Examples.

Synthesis Example 1

The compounds according to the present invention can be synthesized as follows.
(Synthesis of Compound (3))
A compound (3) was synthesized according to the following scheme.

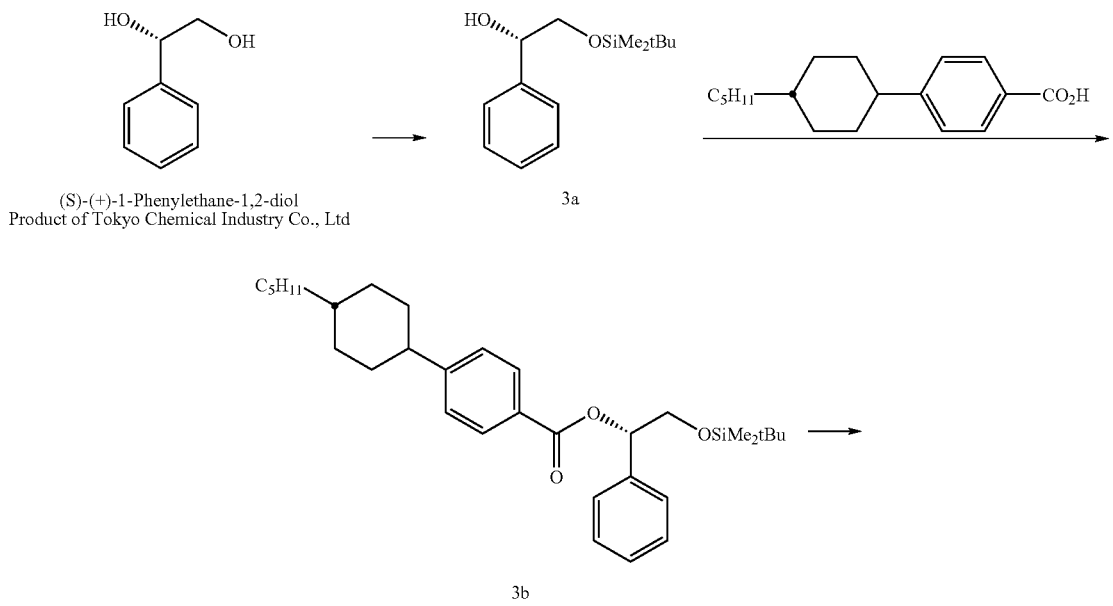

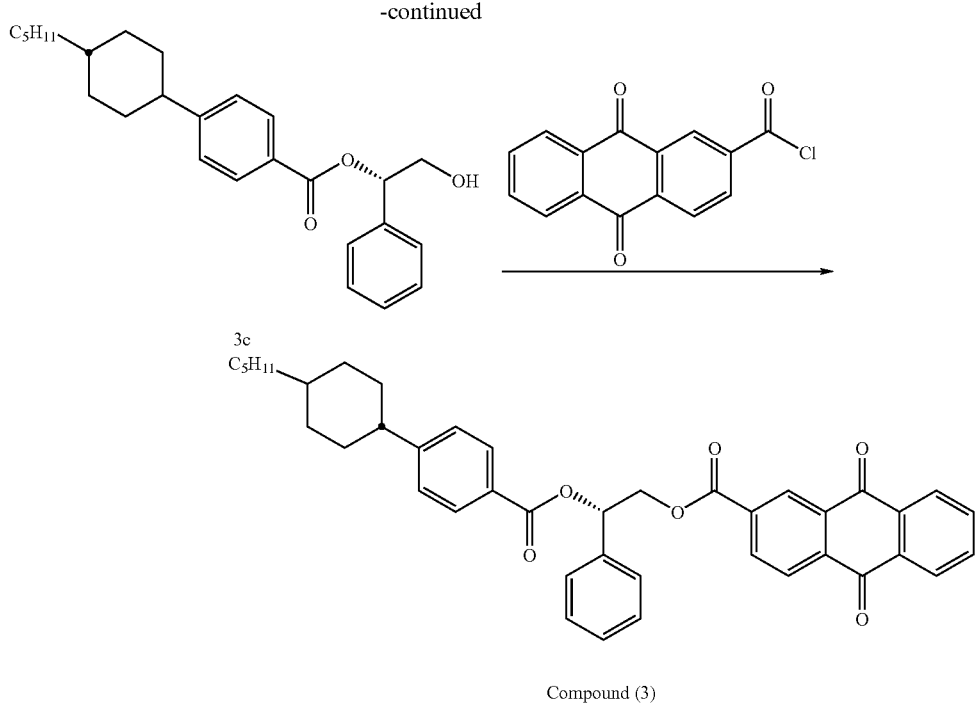

Compound (3)

(Synthesis of Compound 3a)

To a methylene chloride solution (200 ml) containing (s)-(+)-phenylethane-1,2-diol (manufactured by Tokyo Chemical Industry Co., Ltd.) (11.1 g), dimethylaminopyridine (manufactured by Wako Pure Chemical Ind. Ltd.) (10.2 g) and t-butyldimethylsilyl chloride (manufactured by Tokyo Chemical Industry Co., Ltd.) (13.3 g), triethylamine (8.9 g) was added dropwise under ice cooling, and the mixture was stirred at room temperature for 1 hour. The resultant was further stirred for 3 hours under reflux by heating. Thereafter, the reaction liquid was poured in ethyl acetate/1N hydrochloric acid aqueous solution. Then, the organic layer was washed with 1N hydrochloric acid aqueous solution, dried over magnesium sulfate, and then condensed at a reduced pressure. The condensation residue was purified by silica gel column chromatography (developing solvent: ethyl acetate/hexane=1/7), thereby obtaining a compound 3a (15.4 g).

(Synthesis of Compounds 3b and 3c)

To a methylene chloride solution (400 ml) containing the compound 3a (12.0 g), trans-4-pentylcyclohexylbenzoic acid (13.0 g), and dimethylaminopyridine (3.5 g), a methylene chloride solution (30 ml) containing dicyclohexylcarbodiimide (11.8 g) was added dropwise, and stirred under reflux by heating for 2 hours. The reaction liquid was poured in ethyl acetate/1N hydrochloric acid aqueous solution, and filtered. Then, the organic layer was washed with 1N hydrochloric acid aqueous solution, dried over magnesium sulfate, and then condensed at a reduced pressure, thereby obtaining a crude product of a compound 3b.

To a THF solution (50 ml) of the crude product of a compound 3b, a 1M TBAF/THF solution (48 ml) was added dropwise under ice cooling, and the mixture was stirred for 3 hours. The reaction liquid was poured in ethyl acetate/1N hydrochloric acid aqueous solution, and filtered. Then, the organic layer was washed with 1N hydrochloric acid aqueous solution, dried over magnesium sulfate, and then condensed at a reduced pressure. The condensation residue was purified by silica gel column chromatography (developing solvent: ethyl acetate/hexane=1/5), thereby obtaining a compound 3c (13.1 g).

(Synthesis of Compound (3))

To a methylene chloride solution (20 ml) containing the compound 3c (0.5 g), anthraquinone-2-carboxylic acid (manufactured by Tokyo Chemical Industry Co., Ltd.) (0.34 g) and dimethylaminopyridine (97 mg), a methylene chloride solution (5 ml) containing dicyclohexylcarbodiimide (0.32 g) was added dropwise, and the mixture was stirred under reflux by heating for 2 hours. The reaction liquid was poured in ethyl acetate/1N hydrochloric acid aqueous solution, and filtered. Then, the organic layer was washed with 1N hydrochloric acid aqueous solution, dried over magnesium sulfate, and then condensed at a reduced pressure.

The condensation residue was purified by silica gel column chromatography (developing solvent: ethyl acetate/hexane=1/4), and the obtained crude crystals were recrystallized from isopropyl alcohol, thereby obtaining a compound (3) (0.62 g).

The identification of the compound (3) was carried out by elemental analysis, NMR, and MASS spectrum. The appearance was a pale yellow to white solid.

$^1$H-NMR (CDCl$_3$)

δ:0.82-0.94 (3H, t), 0.94-1.14 (2H, m), 1.15-1.51 (11H, m), 1.78-1.92 (4H, d), 2.42-2.56 (1H, ddd), 4.705 (1H, dd), 4.775 (1H, dd), 6.48 (1H, dd), 7.23 (2H, d), 7.34-7.48 (3H, m), 7.53-7.59 (2H, m), 7.81-7.88 (1H, m), 7.84 (1H, d), 7.91 (2H, d), 8.30-8.39 (2H, m), 8.39 (1H, d), 8.47 (1H, dd), 9.01 (1H, sd)

Specific exemplified compounds (1), (2), and (4) to (19) can be similarly synthesized. In the following, $^1$H-NMR data of specific exemplified compounds (1), (2), (4), (9), (10), (12), (16), (17), and (18) will be shown.

Compound (1)

$^1$H-NMR (CDCl$_3$)

δ:0.89 (3H, t), 0.93-1.13 (2H, m), 1.15-1.52 (7H, m), 1.80-1.91 (4H, d), 2.50 (1H, ddd), 4.705 (1H, dd), 4.775 (1H, dd), 6.48 (1H, dd), 7.23 (2H, d), 7.35-7.47 (3H, m), 7.53-7.59 (2H, m), 7.82-7.88 (2H, m), 7.92 (2H, d), 8.31-8.39 (2H, m), 8.39 (1H, d), 8.47 (1H, dd), 9.01 (1H, sd)

Compound (2)

$^1$H-NMR (CDCl$_3$)

δ:0.90 (3H, t), 0.94-1.13 (2H, m), 1.13-1.52 (9H, m), 1.80-1.91 (4H, d), 2.49 (1H, ddd), 4.705 (1H, dd), 4.775 (1H, dd), 6.48 (1H, dd), 7.23 (2H, d), 7.35-7.48 (3H, m), 7.53-7.59 (2H, m), 7.81-7.88 (2H, m), 7.91 (2H, d), 8.30-8.39 (2H, m), 8.39 (1H, d), 8.47 (1H, dd), 9.01 (1H, sd)

Compound (4)

$^1$H-NMR (CDCl$_3$)

δ:0.72-1.43 (21H, m), 1.52-1.80 (7H, m), 1.85-2.00 (2H, m), 2.21 (1H, ddd), 4.475 (1H, dd), 4.54 (1H, dd), 6.33 (1H, dd), 7.35-7.45 (3H, m), 7.47-7.53 (2H, m), 7.82-7.89 (2H, m), 8.32-8.39 (2H, m), 8.41 (1H, d), 8.47 (1H, dd), 9.00 (1H, sd)

Compound (9)

$^1$H-NMR (CDCl$_3$)

δ:0.82-0.94 (3H, t), 0.94-1.14 (2H, m), 1.15-1.53 (11H, m), 1.80-1.92 (4H, d), 2.50 (1H, ddd), 4.67 (1H, dd), 4.76 (1H, dd), 6.41 (1H, dd), 7.26 (2H, d), 7.33-7.46 (5H, m), 7.50-7.57 (2H, m), 7.83-7.90 (2H, m), 7.92 (2H, d), 8.22 (2H, d), 8.33-8.43 (2H, m), 8.48 (1H, d), 8.59 (1H, dd), 9.13 (1H, sd)

Compound (10)

$^1$H-NMR (CDCl$_3$)

δ:0.73-1.45 (21H, m), 1.50-1.82 (7H, m), 1.86-2.01 (2H, m), 2.21 (1H, ddd), 4.405 (1H, dd), 4.55 (1H, dd), 6.27 (1H, dd), 7.32-7.50 (7H, m), 7.83-7.91 (2H, m), 8.21 (2H, d), 8.33-8.42 (2H, m), 8.48 (1H, d), 8.59 (1H, dd), 9.14 (1H, sd)

Compound (12)

$^1$H-NMR (CDCl$_3$)

δ:0.82-0.93 (3H, t), 0.93-1.13 (2H, m), 1.15-1.61 (11H, m), 1.78-1.90 (4H, d), 2.40-2.54 (1H, ddd), 4.04 (5H,$), 4.37-4.42 (2H, dd), 4.54-4.62 (1H, dd), 4.68-4.78 (1H, dd), 4.82-4.87 (2H, ddd), 6.26-6.32 (1H, dd), 7.21-7.29 (2H, d), 7.32-7.46 (3H, m), 7.50-7.57 (2H, d), 7.92-7.98 (2H, d)

Compound (16)

$^1$H-NMR (CDCl$_3$)

δ:0.82-0.94 (3H, t), 0.94-1.14 (2H, m), 1.15-1.57 (11H, m), 1.80-1.94 (4H, d), 2.42-2.56 (1H, ddd), 4.30 (5H, s), 4.51 (2H, dd), 4.60-4.78 (2H, m), 4.96 (2H, ddd), 6.35-6.42 (1H, dd), 7.20-7.30 (5H, dd), 7.32-7.45 (3H, m), 7.48-7.57 (2H, d), 7.86-7.98 (2H, d), 8.15-8.21 (2H, d)

Compound (17)

$^1$H-NMR (CDCl$_3$)

δ:0.82-0.94 (3H, t), 0.94-1.14 (2H, m), 1.15-1.53 (9H, m), 1.80-1.92 (4H, d), 2.50 (1H, ddd), 4.67 (1H, dd), 4.76 (1H, dd), 6.41 (1H, dd), 7.26 (2H, d), 7.33-7.46 (5H, m), 7.50-7.57 (2H, m), 7.83-7.90 (2H, m), 7.92 (2H, d), 8.22 (2H, d), 8.33-8.43 (2H, m), 8.48 (1H, d), 8.59 (1H, dd), 9.13 (1H, sd)

Compound (18)

$^1$H-NMR (CDCl$_3$)

δ:0.90 (3H, t), 0.93-1.12 (2H, m), 1.13-1.53 (17H, m), 1.80-1.91 (4H, d), 2.49 (1H, ddd), 4.705 (1H, dd), 4.775 (1H, dd), 6.48 (1H, dd), 7.23 (2H, d), 7.35-7.47 (3H, m), 7.53-7.59 (2H, m), 7.81-7.88 (2H, m), 7.91 (2H, d), 8.30-8.39 (2H, m), 8.39 (1H, d), 8.47 (1H, dd), 9.01 (1H, sd)

Example 1

Measurement of Oxidation-Reduction Potential

An NMP solution containing 1 mM of each of the specific exemplified compounds and 0.1 M tetrabutylammonium hexafluorophosphate as a supporting electrolyte was subjected to Ar bubbling for 5 minutes, and then cyclic voltammetry measurement was carried out by a potentiostat (660C, manufactured by BAS). The results of the oxidation-reduction potentials 1 and 2 when a working electrode Pt, a counter electrode Pt, and a reference electrode SCE were used are shown in the following table.

TABLE 1

| Compound | Oxidation-reduction potential 1 | Oxidation-reduction potential 2 |
|---|---|---|
| 1 | −0.68 V | −1.42 V |
| 2 | −0.67 V | −1.40 V |
| 3 | −0.62 V | −1.39 V |
| 4 | −0.67 V | −1.42 V |
| 9 | −0.64 V | −1.38 V |
| 10 | −0.65 V | −1.39 V |
| 12 | (+0.46 V) | +0.85 V |
| 16 | (+0.47 V) | +0.84 V |
| 18 | −0.67 V | −1.40 V |

The results of Table 1 have clarified that the exemplified compounds (1), (2), (3), (4), (9), (10), (12), (16), and (18) equivalent to the compound represented by Formula (1) caused an oxidation-reduction reaction.

Example 2

Measurement of Helical Twisting Power (HTP Value)

The exemplified compound (2 mg) according to the present invention was mixed with a host liquid crystal ZLI-2806 (98 mg) (manufactured by Merck), heated on a 160° C. hot plate for 2 hours, cooled to room temperature, and then left over night, thereby producing a chiral nematic liquid crystal composition.

The obtained liquid crystal composition was injected in a wedge-shaped liquid crystal cell (Gap: 1.1 mm, manufactured by EHC), and then observed under a polarization microscope. Then, the pitch length was measured, and the HTP value (Helical Twisting Power) was calculated. The results are shown in Table 2.

The HTP value represents twisting ability (rotation ability) of a chiral reagent to a host liquid crystal agent calculated by the following equation.

$$HTP = 1/(P \times C)$$

(P: Pitch length, C: Content of chiral reagent)

TABLE 2

| Compound | HTP value |
|---|---|
| 1 | 10.1 |
| 2 | 9.7 |
| 3 | 9.5 |
| 4 | 4.0 |
| 9 | 20.7 |
| 10 | 31.2 |
| 12 | 5.5 |
| 16 | 26.6 |
| 17 | 27.9 |
| 18 | 9.2 |

As is clear from Table 2, it is found that the exemplified compounds (1), (2), (3), (4), (9), (10), (12), (16), (17), and (18) equivalent to the compound represented by Formula (1) have a function as a chiral reagent.

Example 3

Measurement of Maximum Absorption Wavelength and Molar Absorption Coefficient 2.5 mg of the exemplified compounds according to the present invention was dissolved in 25 ml of chloroform, thereby preparing sample solutions.

Each sample solution was measured for the UV spectrum in a 1 cm quartz cell using a spectrophotometer UV-2400 (tradename) manufactured by Shimadzu Corp. From the obtained spectrum chart, the maximum absorption wavelength and the molar absorption coefficient were determined. The results are shown in Table 3.

TABLE 3

| Compound | Maximum absorption wavelength (nm) | Molar absorption coefficient ($\epsilon/^{-1}cm^{-1}$) |
| --- | --- | --- |
| 3 | 328.0 | 5690 |
| 4 | 327.5 | 5950 |
| 10 | 326.5 | 6640 |
| 17 | 327.0 | 6930 |

As is clear from Table 3, it is found that the exemplified compound (3) equivalent to the compound represented by Formula (1) has a function as a UV absorber.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A compound represented by the following Formula (1):

Formula (1)

(B)—O
         *
         O-(L)$_x$-(D)$_w$-(L')$_n$-Rd-(B')$_z$
(R)$_v$ wherein, in Formula (1),

* represents an asymmetric carbon atom;

L and L' each independently represent an ether group, an ester group (—COO—, —OCO—), or a carbonyl group (—CO—);

Rd represents an oxidation-reduction reaction causing portion;

D represents a phenylene group (-ph-);

R represents a substituent;

x represents 0 or 1;

z represents an integer of from 0 to 3;

w represents 0 or 1;

n represents 0 or 1;

v represents an integer of from 0 to 5;

when z is 2 or more; a plurality of B's may be the same or different; and when v is 2 or more, a plurality of R's may be the same or different;

B represents alkyl—[cyclohexyl]—[phenyl]—C(=O)—# or alkyl—[cyclohexyl]—[cyclohexyl]—C(=O)—# means a linking portion

B' represents alkyl—[cyclohexyl]—[phenyl]—O—C(=O)—# alkyl—[cyclohexyl]—[cyclohexyl]—O—C(=O)—# alkyl—[cyclohexyl]—CH$_2$—O—[dimethylphenyl]—# or an alkyl group and, wherein the compound of Formula (1) is represented by a compound of Formulae (1-1), (1-2), (1-3), or (1-4):

Formula (1-1)

(B)-O
       *
       O-(L)$_x$-(D)$_w$-(L')$_n$-[anthraquinone with R$^1$, R$^3$, R$^4$, R$^5$, R$^6$, R$^8$ and (B')$_z$]
(R)$_v$ Formula (1-2)

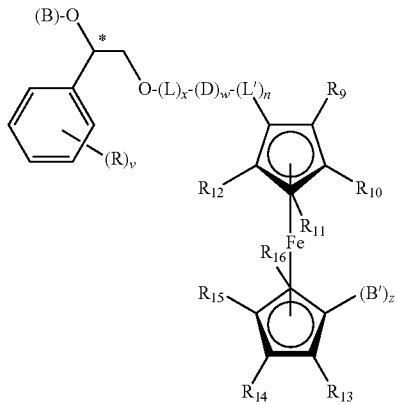

Formula (1-4)

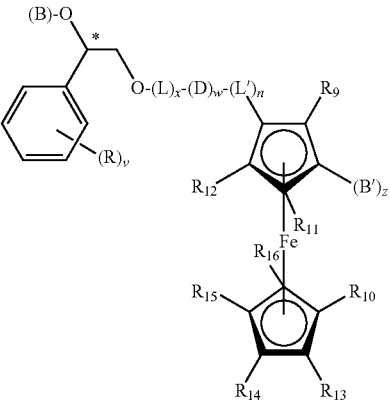

Formula (1-3)

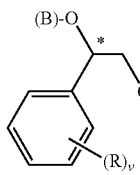

wherein $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, and $R^{16}$ each independently represent a hydrogen atom or a substituent.

2. The compound according to claim 1, wherein the oxidation-reduction potential of the oxidation-reduction reaction causing portion Rd in Formula (1) is from −2.5 V to +2.5 V relative to a reference electrode SCE.

3. The compound according to claim 1, wherein the compound represented by Formula (1) is a compound represented by the following Formula (3-1), (3-2), (3-3), or (3-4):

Formula (3-1)

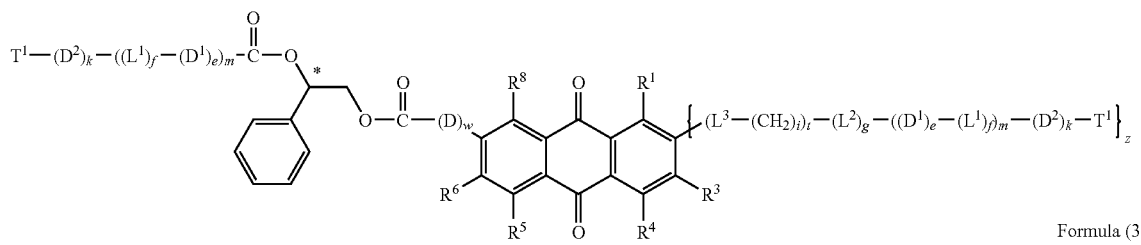

Formula (3-2)

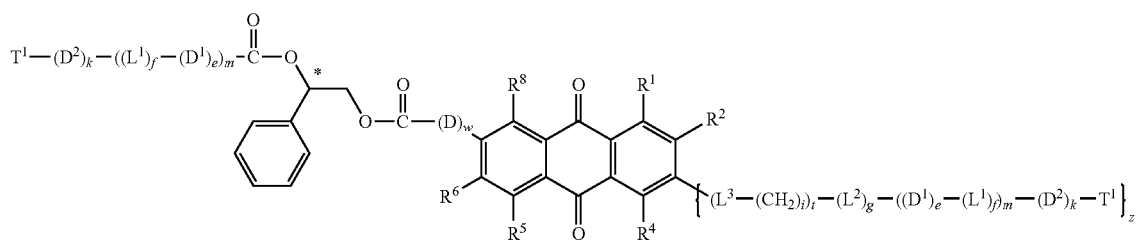

Formula (3-3)

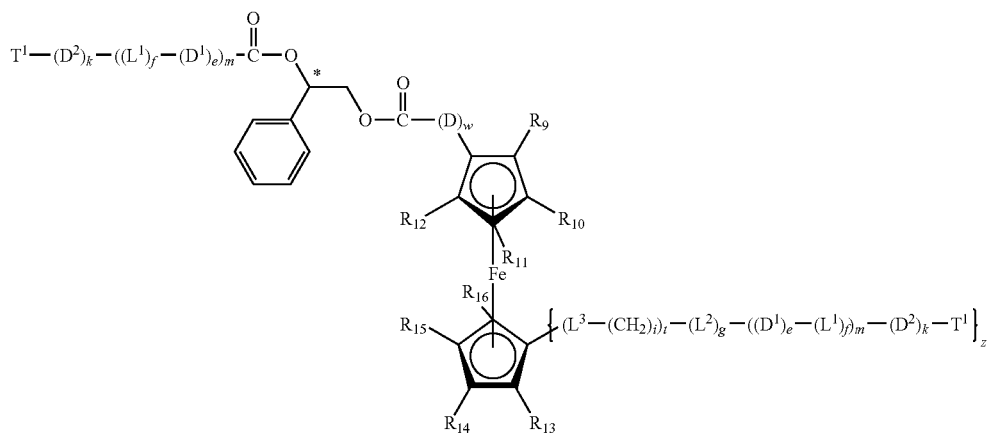

-continued

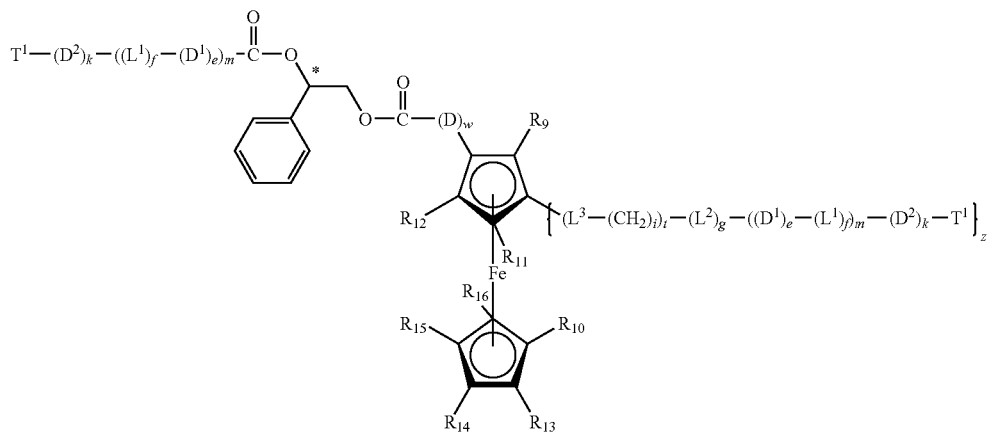

Formula (3-4)

wherein, in Formulae (3-1), (3-2), (3-3), and (3-4), D, w, and z are the same as D, w, and z in Formula (1), respectively; $D^1$ and $D^2$ each independently represent an arylene group, a hetero arylene group, or a divalent alicyclic hydrocarbon group; $L^1$ represents an alkanediyl group, an alkenylene group, an alkynylene group, an ether group, an ester group (—COO—, —OCO—), a carbonyl group, an azo group, (—CH=N—, —N=CH—), an azoxy group, or an alkyleneoxy group; $L^2$ represents an ether group, an ester group (—COO—, —OCO—), or a carbonyl group; $L^3$ represents an ether group, an ester group (—COO—, —OCO—), or a carbonyl group; $T^1$ represents an alkyl group, an alkoxy group, an alkoxycarbonyl group, an acyl group, an acyloxy group, a halogen atom, or a cyano group; e represents an integer of from 1 to 3; f represents an integer of from 0 to 2; m represents an integer of from 1 to 3; k represents 1 or 2; g represents 0 or 1; i represents an integer of from 1 to 20; t represents an integer of from 0 to 4; the total number of the groups represented by $D^1$ and $D^2$ is an integer from 2 to 5; when e or k is 2 or more, two or more groups represented by $D^1$ or $D^2$ may be the same or different; when m is 2 or more, two or more groups represented by $((L^1)_f$-$(D^1)_e)$ may be the same or different; when f is 2, two groups represented by $L^1$ each represent different linking groups; when t is 2 or more, two or more groups represented by $((CH_2)_i$-$L^3)$ each may be the same or different; and $R^1$, $R^2$, $R^3$, $R^4$, $R^5$, $R^6$, $R^8$, $R^9$, $R^1$, $R^{11}$, $R^{12}$, $R^{13}$, $R^{14}$, $R^{15}$, and $R^{16}$ each independently represent a hydrogen atom or a substituent.

4. The compound according to claim 1 wherein: $(L)_x$-$(D)_w$-$(L')_n$ is represented by:

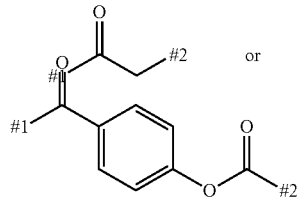

wherein #1 represents a linking portion connected to O, and #2 represents a linking portion connected to Rd.

5. The compound according to claim 1, wherein the compound represented by Formula (1) is one of the following compounds (1) to (19):

(1)

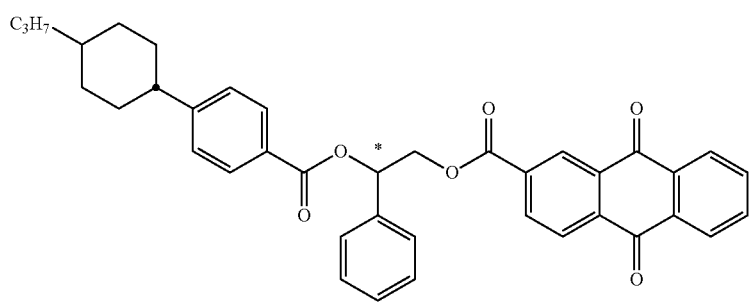

(2)

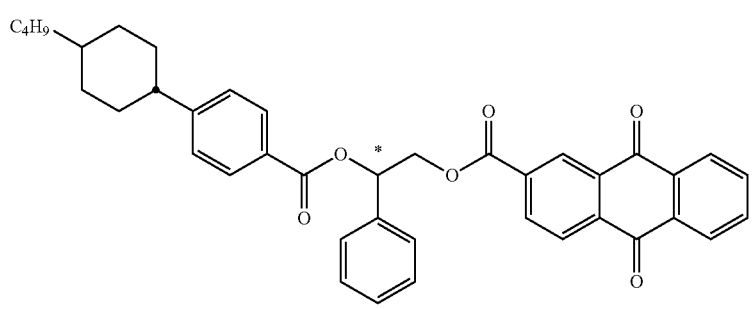

-continued
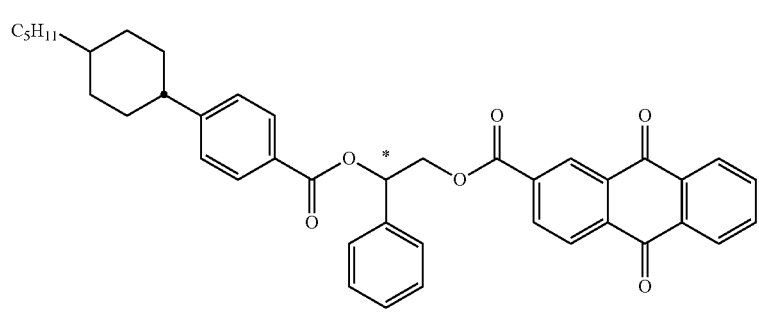
(3)
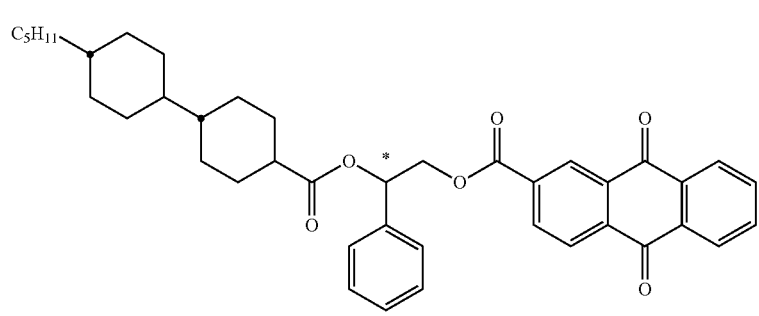
(4)
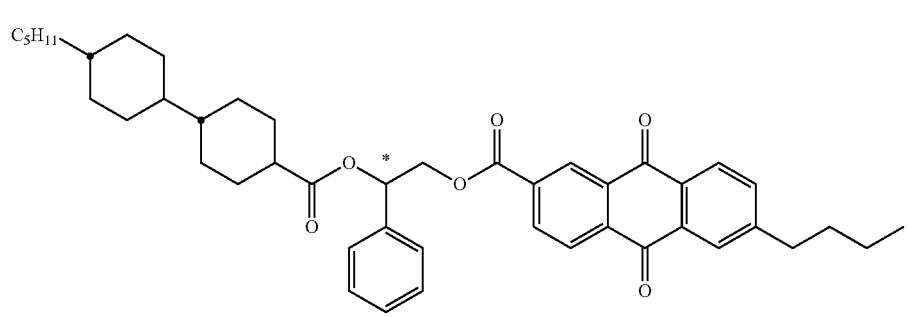
(5)
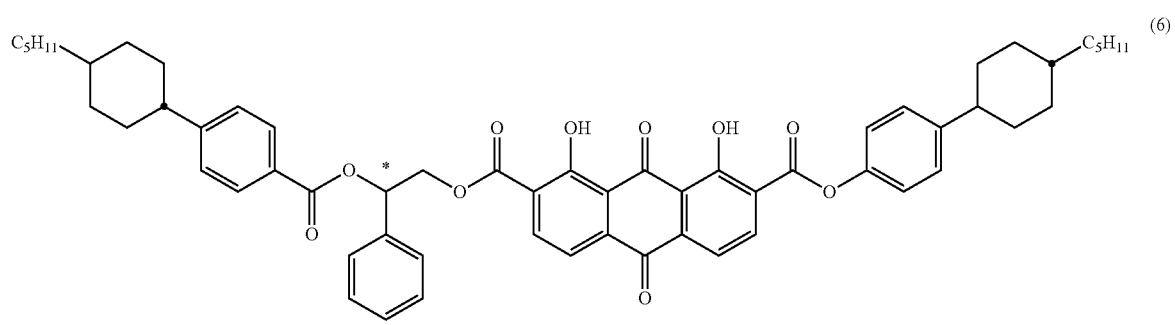
(6)
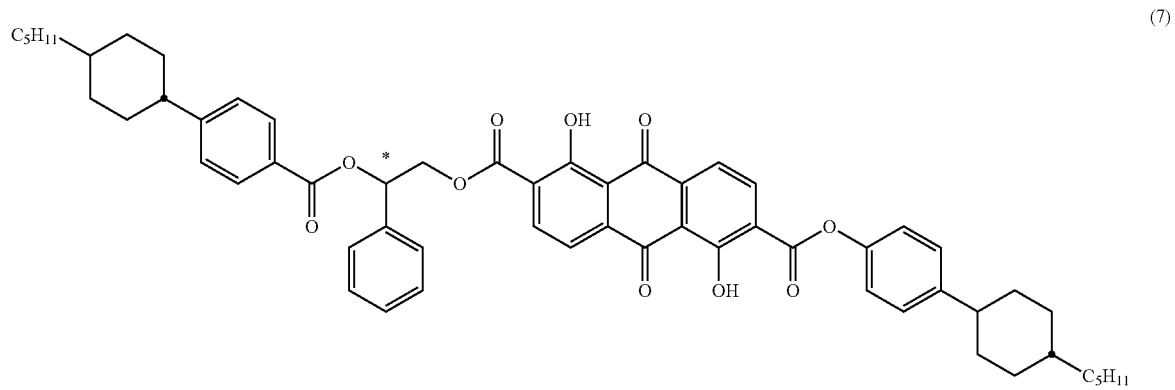
(7)

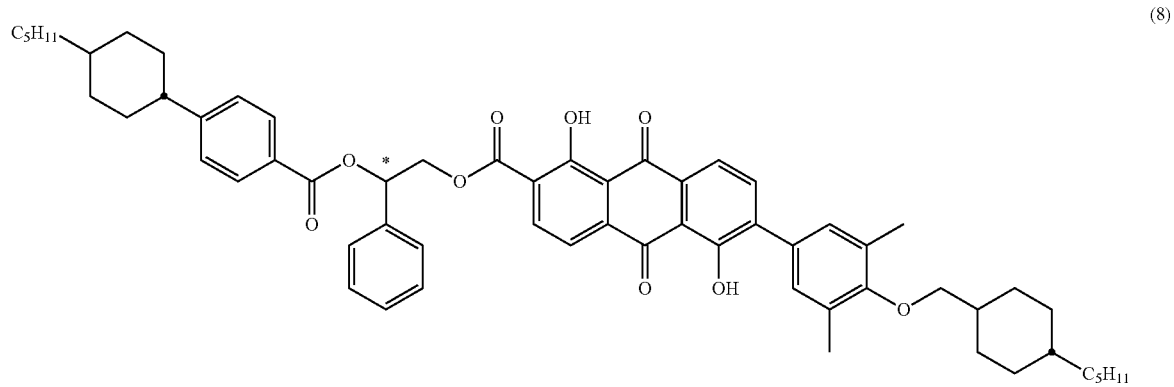
(8)
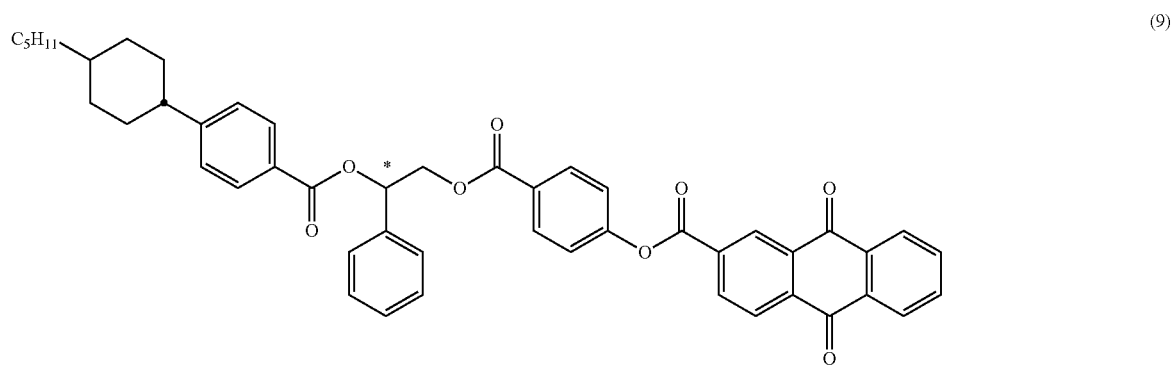
(9)
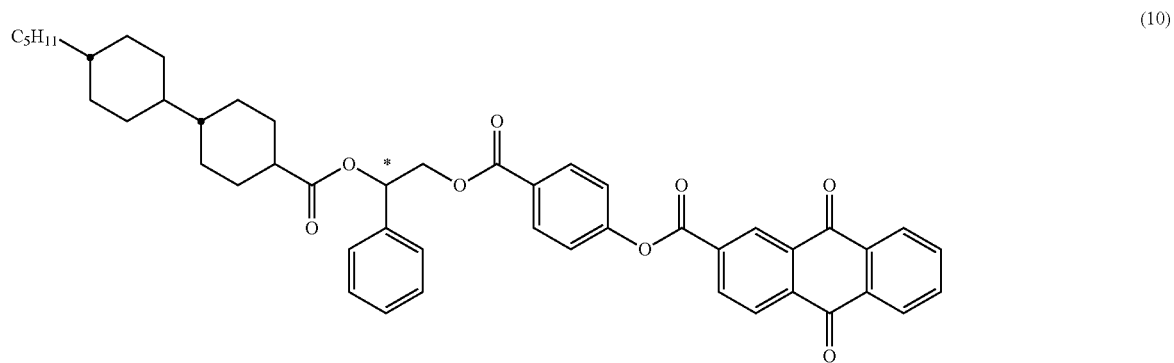
(10)
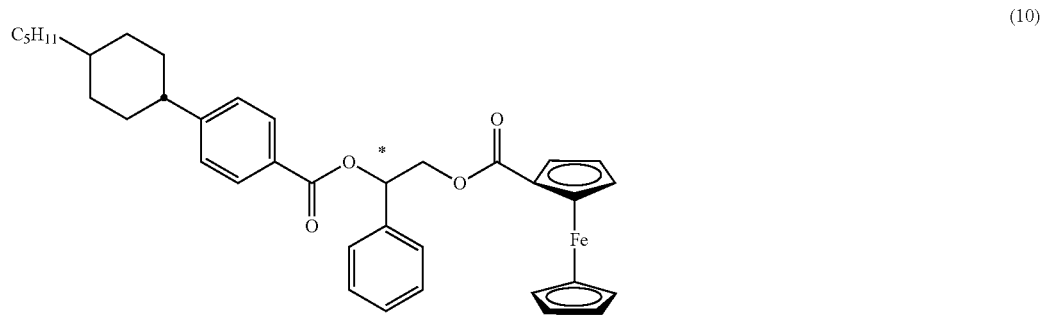
(10)

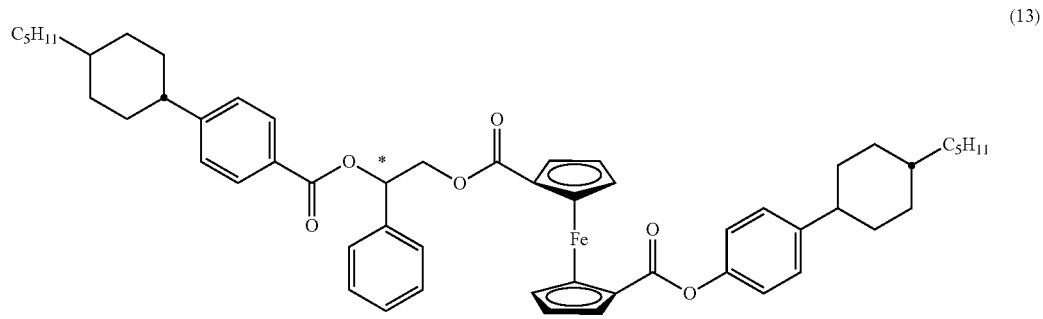
(13)
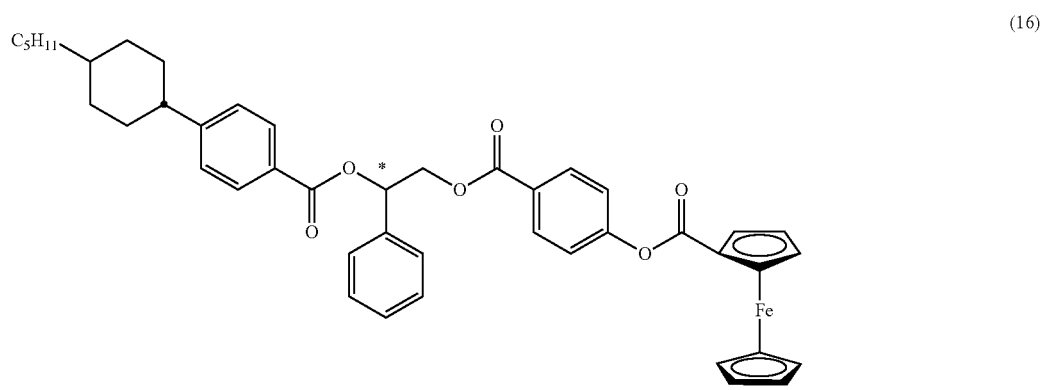
(16)
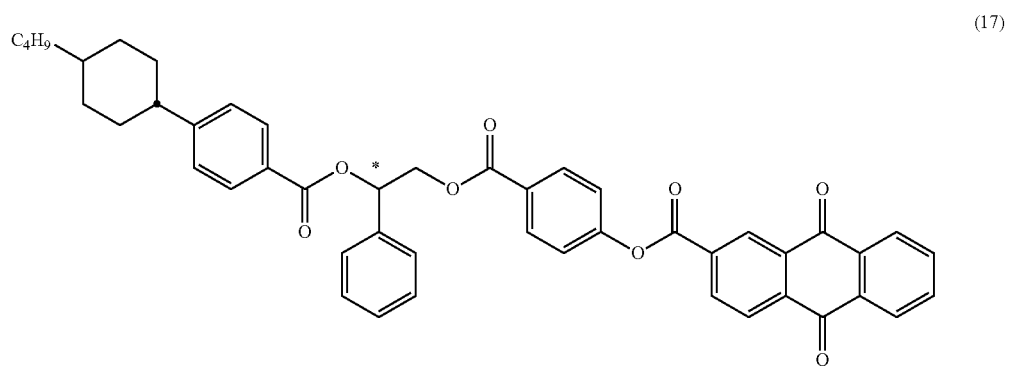
(17)
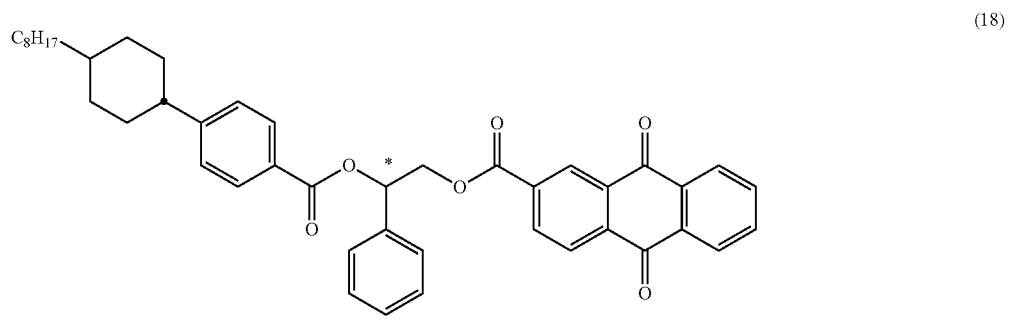
(18)

-continued (19)

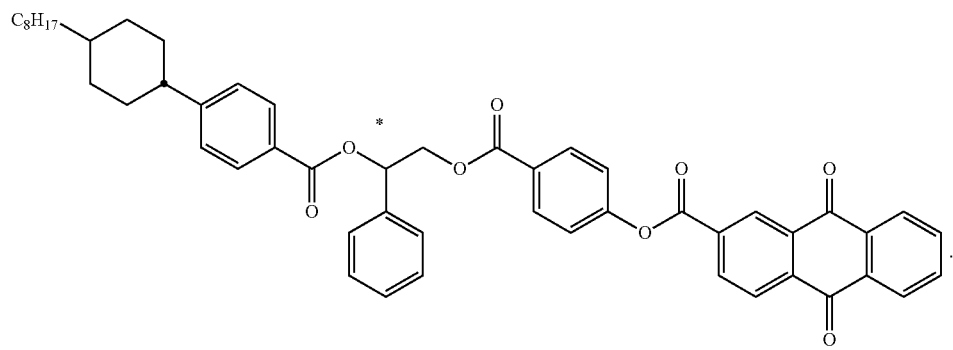

6. A compound represented by the following Formula (1):

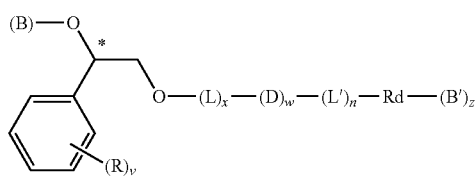

Formula (1)

wherein, in Formula (1),
* represents an asymmetric carbon atom;
L and L' each independently represent an ether group, an ester group (—COO—, —OCO—), or a carbonyl group (—CO—);
Rd represents an oxidation-reduction reaction causing portion;
D represents an arylene group, a hetero arylene group, or a divalent alicyclic hydrocarbon group;
R represents a substituent;
x represents 0 or 1;
z represents an integer of from 0 to 3;
w represents 0 or 1;
n represents 0 or 1;
v represents an integer of from 0 to 5;
when z is 2 or more; a plurality of B's may be the same or different; and when v is 2 or more, a plurality of R's may be the same or different;
B represents

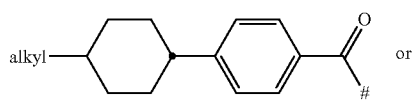 or

\# means a linking portion and,

B' represents

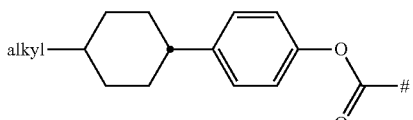

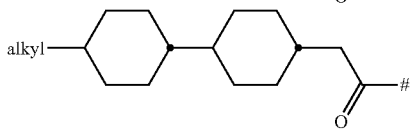

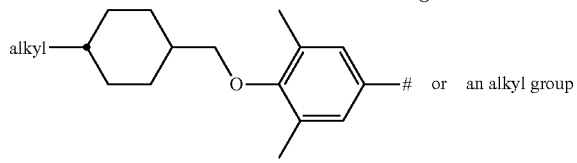 or an alkyl group or an alkyl group wherein the oxidation-reduction potential of the oxidation-reduction reaction causing portion Rd in Formula (1) is from −25 V to +2.5 V relative to a reference electrode SCE.

* * * * *